US012709594B2

(12) United States Patent
Pinto et al.

(10) Patent No.: US 12,709,594 B2
(45) Date of Patent: Aug. 18, 2026

(54) RXFP1 AGONISTS

(71) Applicant: BRISTOL-MYERS SQUIBB COMPANY, Princeton, NJ (US)

(72) Inventors: Donald J. P. Pinto, Churchville, PA (US); Shun Su, San Diego, CA (US); Arvind Mathur, Bridgewater, NJ (US); Michael C. Myers, Newtown, PA (US); Jianqing Li, Guilford, CT (US); Kumar Balashanmuga Pabbisetty, Piscataway, NJ (US); Scott A. Shaw, Lawrence Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 297 days.

(21) Appl. No.: 18/700,868

(22) PCT Filed: Oct. 28, 2022

(86) PCT No.: PCT/US2022/078836

§ 371 (c)(1),
(2) Date: Apr. 12, 2024

(87) PCT Pub. No.: WO2023/077041

PCT Pub. Date: May 4, 2023

(65) Prior Publication Data

US 2024/0417369 A1 Dec. 19, 2024

Related U.S. Application Data

(60) Provisional application No. 63/273,290, filed on Oct. 29, 2021.

(51) Int. Cl.

| | |
|---|---|
| ***C07C 235/14*** | (2006.01) |
| ***A61K 31/167*** | (2006.01) |
| ***A61K 31/17*** | (2006.01) |
| ***A61K 31/192*** | (2006.01) |
| ***A61K 31/424*** | (2006.01) |
| ***C07C 235/74*** | (2006.01) |
| ***C07C 235/84*** | (2006.01) |
| ***C07C 275/34*** | (2006.01) |
| ***C07D 498/04*** | (2006.01) |

(52) U.S. Cl.

CPC .......... *C07C 235/14* (2013.01); *A61K 31/167* (2013.01); *A61K 31/17* (2013.01); *A61K 31/192* (2013.01); *A61K 31/424* (2013.01); *C07C 235/74* (2013.01); *C07C 235/84* (2013.01); *C07C 275/34* (2013.01); *C07D 498/04* (2013.01); *C07C 2602/32* (2017.05)

(58) Field of Classification Search

None

See application file for complete search history.

(56) References Cited

FOREIGN PATENT DOCUMENTS

| | | | |
|---|---|---|---|
| WO | 2011163502 | A1 | 12/2011 |
| WO | 2013165606 | A1 | 11/2013 |
| WO | 2022122773 | A1 | 6/2022 |
| WO | 2023/076626 | A1 | 5/2023 |
| WO | 2023077040 | A1 | 5/2023 |
| WO | 2023077070 | A1 | 5/2023 |

OTHER PUBLICATIONS

Garber_2001, "Relaxin decreases renal interstitial fibrosis and slows progression of renal disease", Kidney International, vol. 59 (2001), pp. 876-882.

Ludwig_2004, "Convenient Synthesis of Pyrrole- and Indolecarboxylic Acid tert-Butylesters", Synthetic Communications, 34:20, 3691-3695.

Mohammed et al., "Coronary Microvascular Rarefaction and Myocardial Fibrosis in Heart Failure With Preserved Ejection Fraction", Circulation, vol. 131, pp. 550-559 (2015).

Roger et al., "Heart Disease and Stroke Statistics—2012 Update", Circulation, vol. 125, e2-220 (2012).

Teerlink_2013, "Serelaxin, recombinant human relaxin-2, for treatment of acute heart failure (RELAX-AHF): a randomised, placebo-controlled trial", The Lancet, vol. 381, Issue 9860 p. 29- 39 Jan. 5, 2013.

Allen, Jr., Loyd V., "Remington: The Science and Practice of Pharmacy, vol. I and vol. II. Twenty-second edition", Pharmaceutical Press, 2012, p. 2724.

Bennett_2014 "Relaxin decreases the severity of established hepatic fibrosis in mice", Liver International 34: 416-426.

Borlaug, et al. "Heart failure with preserved ejection fraction: pathophysiology, diagnosis, and treatment", European Heart Journal (2011) 32, 670-679.

Borlaug_2011 "Diastolic and Systolic Heart Failure Are Distinct Phenotypes Within the Heart Failure Spectrum", vol. 123, Issue 18, May 10, 2011; pp. 2006-2014.

Chen_2018, "Pd-Catalyzed, ortho C—H Methylation and Fluorination of Benzaldehydes Using Orthanilic Acids as Transient Directing Groups"; J. Am. Chem. Soc. 2018, 140, 2789-2792.

(Continued)

*Primary Examiner* — Craig D Ricci

(74) *Attorney, Agent, or Firm* — Hong Liu

(57) ABSTRACT

The disclosure relates to compounds of Formula (I), which are RXFP1 receptor agonists, compositions containing them, and methods of using them, for example, in the treatment of heart failure, fibrotic diseases, and related diseases such as lung disease (e.g., idiopathic pulmonary fibrosis), kidney disease (e.g., chronic kidney disease), or hepatic disease (e.g., non-alcoholic steatohepatitis and portal hypertension).

(I)

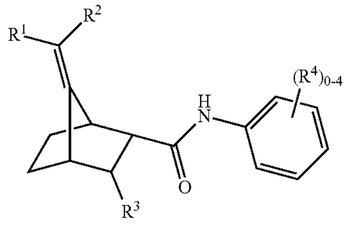

6 Claims, No Drawings

(56) References Cited

OTHER PUBLICATIONS

Clapp et al., "Cardiovascular Function Before, During, and After the First and Subsequent Pregnancies", Am J Cardiol, vol. 80, pp. 1469-1473 (1997).
Conrad et al., "Maternal vasodilation in pregnancy: the emerging role of relaxin", Regul. Integr. Comp. Physiol., vol. 301, pp. R267-R275 (2011).
Dahlke et al "Safety and Tolerability of Serelaxin, a Recombinant Human Relaxin-2 in Development for the Treatment of Acute Heart Failure, inHealthy Japanese Volunteers and a Comparison of Pharmacokinetics and Pharmacodynamics in Healthy Japanese and Caucasian Populations" , The Journal of Clinical Pharmacology , 55(4) 415-422, 2015.
Damman et al., "The Cardiorenal Syndrome in Heart Failure", Progress in Cardiovascular Diseases, vol. 54, pp. 144-154 (2011).
De Keulenaer_2011_"Systolic and Diastolic Heart Failure Are Overlapping Phenotypes Within the Heart Failure Spectrum"; vol. 123, Issue 18, May 10, 2011; pp. 1996-2005.
Greene, T.W. et al., Protecting Groups in Organic Synthesis, 4th Edition, Wiley (2007).
Halls et al., "Relaxin Family Peptide Receptors—former orphans reunite with their parent ligands to activate multiple signalling pathways", British J of Pharmacology, vol. 150, pp. 677-691 (2007).
Halls ML., et al. "Relaxin Activates Multiple CAMP Signaling Pathway Profiles in Different Target Cells", Ann. N Y Acad. Sci., vol. 1160, 108-111 (2009).
Halls, et al., "Relaxin Family Peptide Receptors RXFP1 and RXFP2 Modulate CAMP Signaling by Distinct Mechanisms", vol. 70, pp. 214-226 (2006).
Halls_2009, "RXFP1 Couples to the Gαi3-Gβγ-PI3K-PKCδ Pathway via the Final 10 Amino Acids of the Receptor C-terminal Tail", Annals of the New York Academy of Sciences, 1160, 117-120.
Heidenreich et al., "Forecasting the Future of Cardiovascular Disease in the United States", Circulation, vol. 123, pp. 933-944 (2011).
Hisaw_1926 , "Experimental relaxation of the pubic ligament of the guinea pig", Proc Soc Exp Biol Med 23:661-663.
Hsu et al., "Activation of Orphan Receptors by the Hormone Relaxin", Science, vol. 295, pp. 671-674 (2002).
Jessup et al., "Medical Progress. Heart Failure", The New England Journal of Medicine, vol. 348, pp. 3007-3018 (2003).
Jeyabalan_2010, "Renal Physiology and Pathophysiology in Pregnancy", Renal and Electrolyte Disorders, 2010, pp. 462-518.
Kemp et al., "The pathophysiology of heart failure", Cardiovascular Pathology, vol. 21, pp. 365-371 (2012).
MacMillan_2016, "Silyl Radical Activation of Alkyl Halides in Metallaphotoredox Catalysis: A Unique Pathway for Cross-Electrophile Coupling", J. Am. Chem. Soc. 2016, 138, 8084-8087.
Matsushita, et al.," The Association of Hemoglobin A1c With Incident Heart Failure Among People Without Diabetes: The Atherosclerosis Risk in Communities Study", Diabetes, vol. 59, pp. 2020-2026 (2010).
Millane et al., "ABC of heart failure. Acute and chronic management strategies", BMJ, vol. 320 pp. 559-562 (2000).
Physicians' Desk Reference.
Ponikowski_2014, "A randomized, double-blind, placebo-controlled, multicentre study to assess haemodynamic effects of serelaxin in patients with acute heart failure", European Heart Journal (2014) 35, 431-441.
Poppas et al., "Serial Assessment of the Cardiovascular System in Normal Pregnancy" Circulation, vol. 95(10) pp. 2407-2415 (1997).
Roger V. et al., "Trends in Heart Failure Incidence and Survival in a Community-Based Population", JAMA, vol. 292, pp. 344-350 (2004).
Roger, V.L., "Epidemiology of Heart Failure", Circulation Research , vol. 113(6), pp. 646-659 (2013).
Sherwood et al., "Relaxin's Physiological Roles and Other Diverse Actions", Endocr. Rev. vol. 25, pp. 205-234 2004.
Smith_2006 "Influence of Recombinant Human Relaxin on Renal Hemodynamics in Healthy Volunteers", J Am Soc Nephrol 17: 3192-3197, 2006.
Teichman et al., "Relaxin, a pleiotropic vasodilator for the treatment of heart failure", Heart Fail. Rev., vol. 14, pp. 321-329 (2009).
Unemori_1996, "Relaxin Induces an Extracellular Matrix-degrading Phenotype in Human Lung Fibroblasts In Vitro and Inhibits Lung Fibrosis in a Murine Model In Vivo", J. Clin. Invest, vol. 98, No. 12, Dec. 1996, 2739-2745.
Voors_2014, "Renal Hemodynamic Effects of Serelaxin in Patients With Chronic Heart Failure", vol. 7, Issue 6, Nov. 2014; pp. 994-1002.
Wohlfahrt et al., "Impact of chronic changes in arterial compliance and resistance on left ventricular ageing in humans", Eur. J. Heart Fail., vol. 17, pp. 27-34 (2015).

RXFP1 AGONISTS

CROSS-REFERENCE TO RELATED APPLICATIONS

This application is a 371 application of PCT/US2022/078836, filed Oct. 28, 2022, which claims the benefit of U.S. Provisional Application No. 63/273,290, filed Oct. 29, 2021, the disclosure of which is incorporated herein by reference in its entirety.

BACKGROUND OF THE INVENTION

The present disclosure relates to novel compounds which are relaxin family peptide receptor 1 (RXFP1) agonists, compositions containing them, and methods of using them, for example in the treatment of heart failure, fibrotic diseases, and related diseases such as lung disease (e.g., idiopathic pulmonary fibrosis), kidney disease (e.g., chronic kidney disease), and hepatic disease (e.g., non-alcoholic steatohepatitis and portal hypertension).

The human relaxin hormone (also called relaxin or H2 relaxin) is a 6-kDa peptide composed of 53 amino acids whose activity was initially discovered when Frederick Hisaw in 1926 injected crude extracts from swine corpus luteum into virgin guinea pigs and observed a relaxation of the fibrocartilaginous pubic symphysis joint (Hisaw F L., *Proc. Soc. Exp. Biol. Med.* 1926, 23, 661-663). The relaxin receptor was previously known as Lgr7 but is now officially termed the relaxin family peptide receptor 1 (RXFP1) and was deorphanized as a receptor for relaxin in 2002 (Hsu S Y., et al., *Science,* 2002, 295, 671-674). RXFP1 is reasonably well conserved between mouse and human with 85% amino acid identity and is essentially ubiquitously expressed in humans and in other species (Halls M L., et al., *Br. J. Pharmacol.,* 2007, 150, 677-691). The cell signaling pathways for relaxin and RXFP1 are cell type dependent and quite complex (Halls M L., et al., *Br. J. Pharmacol.,* 2007, 150, 677-691; Halls M L., et al. *Ann. N Y Acad. Sci.,* 2009, 1160, 108-111; Halls M L., *Ann N Y Acad. Sci.,* 2007, 1160, 117-120). The best studied pathway is the relaxin-dependent increase in cellular levels of cAMP in which relaxin functions as an RXFP1 agonist to promote GαS coupling and activation of adenylate cyclase (Halls M L., et al., *Mol. Pharmacol.,* 2006, 70, 214-226).

Since the initial discovery of relaxin much experimental work has focused on delineating the role relaxin has played in female reproductive biology and the physiological changes that occur during mammalian pregnancy (Sherwood O D., *Endocr. Rev.,* 2004, 25, 205-234). During human gestation, in order to meet the nutritional demands imposed upon it by the fetus, the female body undergoes a significant ~30% decrease in systemic vascular resistance (SVR) and a concomitant ~50% increase in cardiac output (Jeyabalan A C., K. P., *Reanl and Electrolyte Disorders.* 2010, 462-518), (Clapp J F. & Capeless E., *Am. J. Cardio.,* 1997, 80, 1469-1473). Additional vascular adaptations include an ~30% increase in global arterial compliance that is important for maintaining efficient ventricular-arterial coupling, as well as an ~50% increase in both renal blood flow (RBF) and glomerular filtration rate (GFR), important for metabolic waste elimination (Jeyabalan A C., K. P., *Reanl and Electrolyte Disorders.* 2010, 462-518), (Poppas A., et al., *Circ.,* 1997, 95, 2407-2415). Both pre-clinical studies in rodents as well as clinical studies performed in a variety of patient settings, provide evidence that relaxin is involved, at least to some extent, in mediating these adaptive physiological changes (Conrad K P., *Regul. Integr. Comp. Physiol.,* 2011, 301. R267-275), (Teichman S L., et al., *Heart Fail. Rev.,* 2009, 14, 321-329). Importantly, many of these adaptive responses would likely be of benefit to HF patients in that excessive fibrosis, poor arterial compliance, and poor renal function are all characteristics common to heart failure patients (Mohammed S F., et al., *Circ.,* 2015, 131, 550-559), (Wohlfahrt P., et al., *Eur. J. Heart Fail.,* 2015, 17, 27-34), (Damman K., et al., *Prog. Cardiovasc. Dis.,* 2011, 54, 144-153).

Heart failure (HF), defined hemodynamically as "systemic perfusion inadequate to meet the body's metabolic demands as a result of impaired cardiac pump function", represents a tremendous burden on today's health care system with an estimated United States prevalence of 5.8 million and greater than 23 million worldwide (Roger V L., et al., *Circ. Res.,* 2013, 113, 646-659). It is estimated that by 2030, an additional 3 million people in the United States alone will have HF, a 25% increase from 2010. The estimated direct costs (2008 dollars) associated with HF for 2010 was $25 billion, projected to grow to $78 B by 2030 (Heidenreich P A., et al., *Circ.,* 2011, 123, 933-944). Astoundingly, in the United States, 1 in 9 deaths has HF mentioned on the death certificate (Roger V L., et al., Circ., 2012, 125, e2-220) and, while survival after HF diagnosis has improved over time (Matsushita K., et al., *Diabetes,* 2010, 59, 2020-2026), (Roger V L., et al., *JAMA,* 2004, 292, 344-350), the death rate remains high with ~50% of people with HF dying within 5 years of diagnosis (Roger V L., et al., *Circ.,* 2012, 125, e2-220), (Roger V L., et al., *JAMA,* 2004, 292, 344-350).

The symptoms of HF are the result of inadequate cardiac output and can be quite debilitating depending upon the advanced stage of the disease. Major symptoms and signs of HF include: 1) dyspnea (difficulty in breathing) resulting from pulmonary edema due to ineffective forward flow from the left ventricle and increased pressure in the pulmonary capillary bed; 2) lower extremity edema occurs when the right ventricle is unable to accommodate systemic venous return; and 3) fatigue due to the failing heart's inability to sustain sufficient cardiac output (CO) to meet the body's metabolic needs (Kemp C D., & Conte J V., *Cardiovasc. Pathol.,* 2011, 21, 365-371). Also, related to the severity of symptoms, HF patients are often described as "compensated" or "decompensated". In compensated heart failure, symptoms are stable, and many overt features of fluid retention and pulmonary edema are absent. Decompensated heart failure refers to a deterioration, which may present as an acute episode of pulmonary edema, a reduction in exercise tolerance, and increasing breathlessness upon exertion (Millane T., et al. *BMJ,* 2000, 320, 559-562).

In contrast to the simplistic definition of poor cardiac performance not being able to meet metabolic demands, the large number of contributory diseases, multitude of risk factors, and the many pathological changes that ultimately lead to heart failure make this disease exceedingly complex (Jessup M. & Brozena S., *N. Engl. J. Med.,* 2003, 348, 3007-2018). Injurious events thought to be involved in the pathophysiology of HF range from the very acute such as myocardial infarction to a more chronic insult such as life-long hypertension. Historically. HF was primarily described as "systolic HF" in which decreased left-ventricular (LV) contractile function limits the expulsion of blood and hence results in a reduced ejection fraction (EF is stroke volume/end diastolic volume), or "diastolic HF" in which active relaxation is decreased and passive stiffness is increased limiting LV filling during diastole, however overall EF is maintained (Borlaug B A. & Paulus W J., *Eur Heart J.,* 2011, 32, 670-679). More recently, as it became understood that diastolic and systolic LV dysfunction was not uniquely specific to these two groups, new terminology was employed: "heart failure with reduced ejection fraction" (HFrEF), and "heart failure with preserved ejection fraction" (HFpEF) (Borlaug B A. & Paulus W J., *Eur Heart J.,* 2011, 32, 670-679). Although these two patient populations have very similar signs and symptoms, whether HFrEF and HFpEF represent two distinct forms of HF or two extremes of a single spectrum sharing a common pathogenesis is currently under debate within the cardiovascular community (Borlaug B A. & Redfield M M., *Circ.,* 2011, 123, 2006-2013), (De Keulenaer G W., & Brutsaert D L., *Circ.,* 2011, 123, 1996-2004).

Serelaxin, an intravenous (IV) formulation of the recombinant human relaxin peptide with a relatively short first-phase pharmacokinetic half-life of 0.09 hours, is currently being developed for the treatment of HF (Novartis, 2014). Serelaxin has been given to normal healthy volunteers (NHV) and demonstrated to increase RBF (Smith M C., et al., *J. Am. Voc. Nephrol.* 2006, 17, 3192-3197) and estimated GFR (Dahlke M., et al., *J. Clin. Pharmacol.,* 2015, 55, 415-422). Increases in RBF were also observed in stable compensated HF patients (Voors A A., et al., *Cir. Heart Fail.,* 2014, 7, 994-1002). In large clinical studies, favorable changes in worsening renal function, worsening HF, as well as fewer deaths, were observed in acute decompensated HF (ADHF) patients in response to an in-hospital 48 hour IV infusion of serelaxin (Teerlink J R., et al., *Lancet,* 2013, 381, 29-39), (Ponikowski P., et al., *Eur. Heart,* 2014, 35, 431-441). Suggesting that chronic dosing of serelaxin could provide sustained benefit to HF patients, improvement in renal function based on serum creatinine levels was observed in scleroderma patients given serelaxin continuously for 6 months using a subcutaneous pump (Teichman S L., et al., *Heart Fail. Rev.,* 2009, 14, 321-329). In addition to its potential as a therapeutic agent for the treatment of HF, continuous subcutaneous administration of relaxin has also been demonstrated to be efficacious in a variety of animal models of lung (Unemori E N., et al. *J. Clin. Invet.,* 1996, 98, 2739-2745), kidney (Garber S L., et al., *Kidney Int.,* 2001, 59, 876-882), and liver injury (Bennett R G., *Liver Int.,* 2014, 34, 416426).

In summary, a large body of evidence supports a role for relaxin-dependent agonism of RXFP1 mediating the adaptive changes that occur during mammalian pregnancy, and that these changes translate into favorable physiological effects and outcomes when relaxin is given to HF patients. Additional preclinical animal studies in various disease models of lung, kidney, and liver injury provide evidence that relaxin, when chronically administered, has the potential to provide therapeutic benefit for multiple indications in addition to HF. More specifically, chronic relaxin administration could be of benefit to patients suffering from lung disease (e.g., idiopathic pulmonary fibrosis), kidney disease (e.g., chronic kidney disease), or hepatic disease (e.g., non-alcoholic steatohepatitis and portal hypertension).

SUMMARY OF THE INVENTION

The present invention provides novel substituted norbornyl compounds, their analogues, including stereoisomers, tautomers, pharmaceutically acceptable salts, or solvates thereof, which are useful as RXFP1 receptor agonists.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used, for example, in the treatment and/or prophylaxis of heart failure, fibrotic diseases, and related diseases, such as; lung disease (e.g., idiopathic pulmonary fibrosis), kidney disease (e.g., chronic kidney disease), or hepatic disease (e.g., non-alcoholic steatohepatitis and portal hypertension).

The compounds of the present invention may be used in therapy.

The compounds of the present invention may be used for the manufacture of a medicament for the treatment and/or prophylaxis of heart failure.

The compounds of the invention can be used alone, in combination with other compounds of the present invention, or in combination with one or more, preferably one to two other agent(s).

These and other features of the invention will be set forth in expanded form as the disclosure continues.

DESCRIPTION OF THE INVENTION

The invention encompasses compounds of Formula (I), which are RXFP1 receptor agonists, compositions containing them, and methods of using them.

In a first aspect, the present invention provides, inter alia, compounds of Formula (I):

(I)

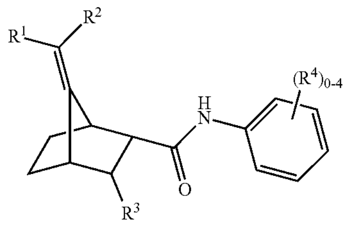

or pharmaceutically acceptable salts thereof, wherein:

$R^1$ is halo, CN, $C_{1-7}$ alkyl substituted with 0-3 $R^6$, $C_{2-7}$ alkenyl substituted with 0-3 $R^6$, $C_{2-7}$ alkynyl substituted with 0-3 $R^6$, $C_{3-6}$ cycloalkyl substituted with 0-3 $R^{14}$, $C_{3-6}$ cycloalkenyl substituted with 0-3 $R^{14}$, aryl substituted with 0-3 $R^{14}$, or 4- to 6-membered heterocyclyl comprising 1-3 heteroatoms selected from O, $S(=O)_p$, N, and $NR^{14a}$ and substituted with 0-3 $R^{14}$;

$R^2$ is H or $C_{1-3}$ alkyl;

$R^3$ is $—NR^aC(=O)R^5$, $—NR^aC(=O)(CR^dR^d)_{1-2}R^7$, or $—NR^aC(=O)NR^8R^7$;

$R^4$ is halo, CN, $C_{1-4}$ alkyl substituted with 0-5 halo substituents, —OH, $—OC_{1-4}$ alkyl substituted with 0-5 halo substituents, $—S(=O)_pR^c$, or aryl;

$R^5$ is $C_{1-8}$alkyl substituted with 0-4 $R^{11}$ or $C_{3-6}$ cycloalkyl substituted with 0-4 $R^8$ and 0-2 $R^9$;

$R^6$ is halo, OH, $C_{3-6}$ cycloalkyl, or aryl;

$R^7$ is aryl substituted with 0-4 $R^8$ and 0-2 $R^9$;

$R^8$ is $—OR^b$;

$R^9$ is halo, CN, phenyl substituted with 0-3 $R^{10}$ and 0-2 $R^{11}$, or 3- to 12-membered heterocyclyl comprising 1-5 heteroatoms selected from O, S(═O)$_p$, N, and NR$^{11a}$, and substituted with 0-3 R$^{10}$ and 0-2 R$^{11}$;

R$^{10}$ is halo, CN, or C$_{1-4}$ alkyl;

R$^{11}$ is C$_{1-3}$ alkyl substituted with 0-1 R$^{12}$ and 0-1 R$^{13}$, —OR$^b$, —NR$^a$R$^a$, —NR$^a$C(═O)R$^b$, —NR$^a$C(═O)OR$^b$, —NR$^a$C(═O)NR$^a$R$^a$, —NR$^a$S(═O)$_p$R$^c$, —C(═O)R$^b$, —C(═O)OR$^b$, —C(═O)NR$^a$R$^a$, —C(═O)NR$^a$S(═O)$_p$R$^c$, —OC(═O)R, —S(═O)$_p$R$^c$, —S(═O)$_p$NR$^a$R$^a$, C$_{3-10}$ carbocyclyl substituted with 0-5 R$^e$, 4- to 6-membered heterocyclyl comprising 1-4 heteroatoms selected from O, S(═O)$_p$, N and NR$^{15}$, and substituted with 0-5 R$^e$;

R$^{11a}$ is H, or C$_{1-4}$ alkyl substituted with 0-2 R$^e$;

R$^{12}$ is halo, —C(═O)OR$^b$, —C(═O)NHR$^a$, —C(═O)NHOR$^b$, or C$_{1-4}$ alkyl substituted with 0-3 halo or OH substituents;

R$^{13}$ is —OR$^b$, —NR$^a$R$^a$, —NR$^a$C(═O)R$^b$, —NR$^a$C(═O)OR, —NR$^a$S(═O)$_p$R$^c$, —NR$^a$S(O)$_p$NR$^a$R$^a$, —OC(═O)NR$^a$R$^a$, —OC(═O)NR$^a$OR$^b$, —S(═O)$_p$NR$^a$R$^a$, or —S(O)$_p$R$^c$;

R$^{14}$ is halo, CN, C$_{1-4}$ alkyl substituted with 0-3 halo substituents, —OC$_{1-4}$ alkyl substituted with 0-3 halo substituents, —(CH$_2$)$_{0-3}$—NR$^a$R$^a$, —(CH$_2$)$_{0-3}$-aryl substituted with 0-3 R$^e$, —O-aryl substituted with 0-3 R$^e$, or —(CH$_2$)$_{0-3}$-3- to 12-membered heterocyclyl comprising 1-4 heteroatoms selected from O, S(═O)$_p$, and N, and substituted with 0-3 R$^e$;

R$^{14a}$ is H, C(═O)C$_{1-4}$ alkyl, or C$_{1-3}$ alkyl substituted with 0-3 aryl substituents substituted with 0-2 halo substituents;

R$^{15}$ is H, C$_{1-3}$ alkyl, or aryl;

R$^{16}$ is C$_{1-3}$ alkyl substituted with 0-1 R$^e$. —C(═O)R$^b$, —C(═O)OR$^b$, —C(═O)NR$^a$R$^a$, —C(═O)NR$^a$S(═O)$_p$R$^c$, —OC(═O)R$^b$, —S(═O)$_p$R$^c$, or —S(═O)$_p$NR$^a$R$^a$;

R$^a$ is H, C$_{1-5}$ alkyl substituted with 0-5 R$^e$, C$_{2-5}$ alkenyl substituted with 0-5 R$^e$, C$_{2-5}$ alkynyl substituted with 0-5 R$^c$, —(CH$_2$)$_n$—C$_{3-10}$ carbocyclyl substituted with 0-5 R$^e$, or —(CH$_2$)$_n$-3- to 12-membered heterocyclyl comprising 1-4 heteroatoms selected from O, S(═O)$_p$, and N, and substituted with 0-5 R$^e$; or R$^a$ and R$^a$ together with the nitrogen atom to which they are both attached form a 3- to 12-membered heterocyclyl comprising 1-4 heteroatoms selected from O, S(═O)$_p$, and N, substituted with 0-5 R$^e$;

R$^b$ is H, C$_{1-5}$ alkyl substituted with 0-5 R$^e$, C$_{2-5}$ alkenyl substituted with 0-5 R$^e$, C$_{2-5}$ alkynyl substituted with 0-5 R$^c$, —(CH$_2$)$_n$—C$_{3-10}$ carbocyclyl substituted with 0-5 R$^e$, or —(CH$_2$)$_n$-3- to 12-membered heterocyclyl comprising 1-4 heteroatoms selected from O, S(═O)$_p$, and N, and substituted with 0-5 R$^e$;

R$^c$ is C$_{1-5}$ alkyl substituted with 0-5 R$^e$, C$_{2-5}$ alkenyl substituted with 0-5 R$^e$, C$_{2-5}$ alkynyl substituted with 0-5 R$^e$, C$_{3-6}$ carbocyclyl, or 3- to 12-membered heterocyclyl comprising 1-4 heteroatoms selected from O, S(═O)$_p$, and N;

R$^d$ is H, —OR$^b$, or C$_{1-5}$ alkyl substituted with 0-5 R$^e$;

R$^e$ is halo, CN, ═O, C$_{1-6}$ alkyl substituted with 0-5 R$^g$, C$_{2-6}$ alkenyl substituted with 0-5 R$^g$, C$_{2-6}$ alkynyl substituted with 0-5 R$^g$, —(CH$_2$)$_n$—C$_{3-10}$ carbocyclyl substituted with 0-5 R$^g$, —(CH$_2$)$_n$-3- to 12-membered heterocyclyl comprising 1-4 heteroatoms selected from O, S(═O)$_p$, and N, and substituted with 0-5 R$^g$, —(CH$_2$)$_n$OR$^f$, —C(═O)OR$^f$, —C(═O)NR$^f$R$^f$, —NR$^f$C(═O)R$^f$, —S(═O)$_p$R$^f$, —NR$^f$C(═O)OR$^f$, —OC(═O)NR$^f$R$^f$, or —(CH$_2$)$_n$NR$^f$R$^f$;

R$^f$ is H, C$_{1-5}$ alkyl, C$_{3-6}$ cycloalkyl, or aryl; or R$^f$ and R$^f$ together with the nitrogen atom to which they are both attached form a 3- to 12-membered heterocyclyl comprising 1-4 heteroatoms selected from O, S(═O)$_p$, and N, and;

R$^g$ is halo, CN, OH, C$_{1-6}$ alkyl, C$_{3-6}$ cycloalkyl, or aryl;

n is zero, 1, 2, or 3; and p is zero, 1, or 2.

In a second aspect within the scope of the first aspect, the present invention provides compounds of Formula (II)

(II)

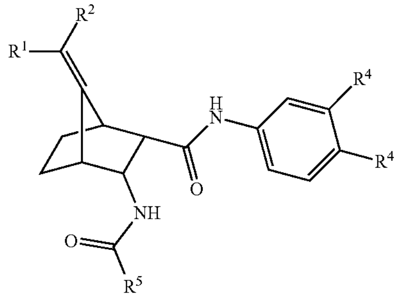

or pharmaceutically acceptable salts thereof, wherein:

R$^1$ is halo, C$_{1-4}$ alkyl substituted with 0-4 halo substituents. C$_{3-6}$ cycloalkyl, or phenyl;

R$^2$ is H;

R$^4$ is halo or C$_{1-4}$ alkyl substituted with 0-4 halo substituents;

R$^5$ is C$_{3-6}$ cycloalkyl substituted with 0-1 R$^9$;

R$^9$ is halo, CN, or phenyl substituted with 0-1 R$^{10}$ and 0-1 R$^{11}$,

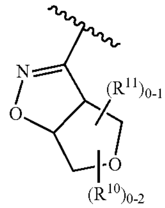 , 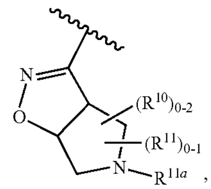 , or 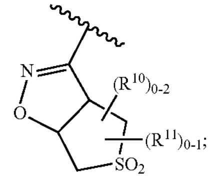

R$^{10}$ is halo, CN, or C$_{1-4}$ alkyl;

R$^{11}$ is —OH, —OC$_{1-4}$ alkyl, or —C(═O)OR$^b$;

R$^{11a}$ is H or C$_{1-3}$ alkyl;

R$^a$ is H or C$_{1-4}$ alkyl; and

R$^b$ is H or C$_{1-4}$ alkyl.

In a third aspect within the scope of the first to third aspects, the present invention provides compounds of Formula (II):

(II)

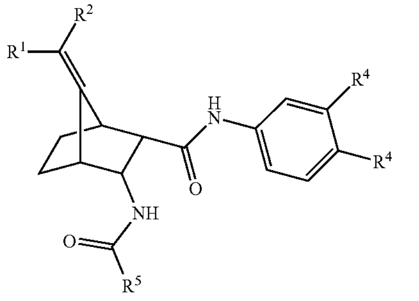

or pharmaceutically acceptable salts thereof, wherein:

$R^1$ is halo, $C_{1-4}$ alkyl substituted with 0-4 halo substituents, $C_{3-6}$ cycloalkyl, or phenyl;

$R^2$ is H;

$R^4$ is halo or $C_{1-4}$ alkyl substituted with 0-4 halo substituents;

$R^5$ is $C_{1-7}$ alkyl substituted with 0-1 $R^{11}$;

$R^{11}$ is —$OR^b$, —$C(=O)R^b$, —$C(=O)OR^b$, or —$C(=O)NR^aR^a$;

$R^a$ is H or $C_{1-4}$ alkyl; and $R^b$ is H or $C_{1-4}$ alkyl.

In a fourth aspect within the scope of the first aspect, the present invention provides compounds of Formula (III):

(III)

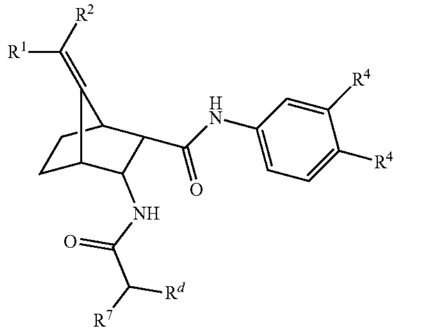

or pharmaceutically acceptable salts thereof, wherein:

$R^1$ is halo, $C_{1-4}$ alkyl substituted with 0-4 halo substituents. $C_{3-6}$ cycloalkyl, or phenyl;

$R^2$ is H;

$R^4$ is halo or $C_{1-4}$ alkyl substituted with 0-4 halo substituents;

$R^7$ is aryl substituted with 0-1 $R^8$ and 0-1 $R^9$;

$R^8$ is —$OR^b$;

$R^9$ is halo, CN, or phenyl substituted with 0-3 $R^{10}$ and 0-2 $R^{11}$;

$R^{10}$ is halo, CN, $C_{1-4}$ alkyl, —OH, or —$OC_{1-4}$ alkyl;

$R^{11}$ is —$OR^b$ or —$C(=O)OR^b$;

$R^a$ is H or $C_{1-4}$ alkyl;

$R^b$ is H, $C_{1-4}$ alkyl, or phenyl; and $R^d$ is —OH or —$OC_{1-4}$ alkyl.

In a fifth aspect within the scope of the first aspect, the present invention provides compounds of Formula (IV):

(IV)

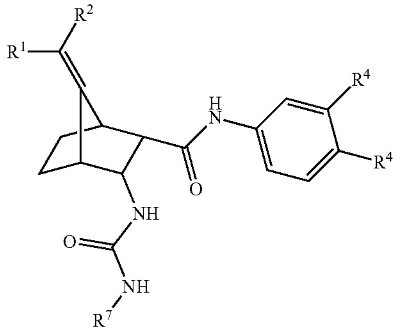

or pharmaceutically acceptable salts thereof, wherein:

$R^1$ is halo, $C_{1-4}$ alkyl substituted with 0-4 halo substituents. $C_{3-6}$ cycloalkyl, or phenyl;

$R^2$ is H;

$R^4$ is halo or $C_{1-4}$ alkyl substituted with 0-4 halo substituents;

$R^7$ is aryl substituted with 0-1 $R^8$ and 0-1 $R^9$ $R^8$ is —$OC_{1-4}$ alkyl substituted with 0-5 halo or OH substituents;

$R^9$ is halo, CN, or phenyl substituted with 0-3 $R^{10}$ and 0-2 $R^{11}$;

$R^{10}$ is halo, CN, $C_{1-4}$ alkyl, —OH, or —$OC_{1-4}$ alkyl;

$R^{11}$ is —$OR^b$ or —$C(=O)OR^b$;

$R^a$ is H or $C_{1-4}$ alkyl; and $R^b$ is H, $C_{1-4}$ alkyl, or phenyl.

For a compound of Formula (I), the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{11a}$, $R^{12}$, $R^{13}$, $R^{14}$, $R^{14a}$, $R^{15}$, $R^a$, $R^b$, $R^c$, $R^d$, $R^e$, $R^f$, and $R^g$ can be used independently with the scope of any other instance of a variable substituent. As such, the invention includes combinations of the different aspects.

Unless specified otherwise, these terms have the following meanings.

"Halo" includes fluoro, chloro, bromo, and iodo.

"Alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "Co alkyl" or "Co alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

"Carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocyclyls include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocyclyl (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. When the term "carbocyclyl" is used, it is intended to include "aryl," "cycloalkyl," and "spirocycloalkyl." Preferred carbocyclyls, unless otherwise specified, are cyclopropyl, cyclobutyl, cyclopentyl, cyclohexyl, phenyl, and indanyl.

"Cycloalkyl" is intended to mean cyclized alkyl groups, including mono-, bi- or multicyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl.

"Spirocycloalkyl" is intended to mean hydrocarbon bicyclic ring systems with both rings connected through a single atom. The ring can be different in size and nature, or identical in size and nature. Examples include spiropentane, spirohexane, spiroheptane, spirooctane, spirononane, or spirodecane.

"Bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary,* 13th Edition, John Wiley & Sons, Inc., New York (1997).

"Benzyl" is intended to mean a methyl group on which one of the hydrogen atoms is replaced by a phenyl group, wherein said phenyl group may optionally be substituted with 1 to 5 groups, preferably 1 to 3 groups.

"Heterocycle", "heterocyclyl" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N. O and S, and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. Bridged rings are also included in the definition of heterocyclyl. When the term "heterocyclyl" is used, it is intended to include heteroaryl.

Examples of heterocyclyls include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazoyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl. 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocyclyls.

"Bicyclic heterocyclyl" "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocyclyl, a 6-membered heterocyclyl or a carbocyclyl (provided the first ring is not benzo when the second ring is a carbocyclyl).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocyclyl exceeds 1, then these heteroatoms are not adjacent to one another. It is preferred that the total number of S and O atoms in the heterocyclyl is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydroquinoxalinyl, and 1,2,3,4-tetrahydroquinazolinyl.

"Heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The invention includes all tautomeric forms of the compounds, atropisomers and rotational isomers.

All processes used to prepare compounds of the present invention and intermediates made therein are considered to be part of the present invention.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry,* 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

RXFP1 Cyclic Adenosine Monophosphate (cAMP) Assays. Human embryonic kidney cells 293 (HEK293) cells and HEK293 cells stably expressing human RXFP1, were cultured in MEM medium supplemented with 10% qualified FBS, and 300 μg/ml hygromycin (Life Technologies). Cells were dissociated and suspended in assay buffer. The assay buffer was HBSS buffer (with calcium and magnesium) containing 20 mM HEPES. 0.05% BSA, and 0.5 mM IBMX. Cells (3000 cells per well, except 1500 cell per well for HEK293 cells stably expressing human RXFP1) were added to 384-well Proxiplates (Perkin-Elmer). Cells were immediately treated with test compounds in DMSO (2% final) at final concentrations in the range of 0.010 nM to 50 μM. Cells were incubated for 30 min at room temperature. The level of intracellular cAMP was determined using the HTRF HiRange cAMP assay reagent kit (Cisbio) according to manufacturer's instructions. Solutions of cryptate conjugated anti-cAMP and d2 fluorophore-labelled cAMP were made in a supplied lysis buffer separately. Upon completion of the reaction, the cells were lysed with equal volume of the d2-cAMP solution and anti-cAMP solution. After a 1 h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 2.7 μM to 0.1 μM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the human RXFP1 (hRXFP1) HEK293 cAMP assay described above and found to have agonist activity. Table I lists $EC_{50}$ values in the hRXFP1 HEK293 cAMP assay measured for the examples.

TABLE 1

| Example | cAMP hRXFP1 HEK293 Assay $EC_{50}$ (nM) |
|---|---|
| 1 | 930 |
| 2 | 300 |
| 3 | 510 |
| 4 | 3,800 |
| 5 | 1,200 |
| 6 | 3,300 |
| 7 | 3,400 |
| 8 | 4,700 |
| 9 | 510 |
| 10 | 2,000 |
| 11 | 4,300 |
| 12 | 350 |
| 13 | 2,900 |
| 14 | 1,600 |
| 15 | 1,400 |
| 16 | 1,000 |
| 17 | 1,600 |
| 18 | 1,000 |
| 19 | 2,000 |

Pharmaceutical Compositions and Methods of Use

The compounds of Formula (I) are RXFP1 receptor agonists and may find use in the treatment of medical indications such as heart failure (e.g., HFREF and HFpEF), fibrotic diseases, and related diseases such as lung disease (e.g., idiopathic pulmonary fibrosis or pulmonary hypertension), kidney disease (e.g., chronic kidney disease), or hepatic disease (e.g., non-alcoholic steatohepatitis and portal hypertension). The compounds of Formular (I) can also be used to treat disorders that are a result of or a cause of arterial stiffness, reduced arterial elasticity, reduced arterial compliance and distensibility including hypertension, kidney disease, peripheral arterial disease, carotid and cerebrovascular disease (i.e stroke and dementia), diabetes, microvascular disease resulting in end organ damage, coronary artery disease, and heart failure. The compounds described herein may also be used in the treatment of pre-eclampsia.

Another aspect of the invention is a pharmaceutical composition comprising a compound of Formula (I) and a pharmaceutically acceptable carrier.

Another aspect of the invention is a pharmaceutical composition comprising a compound of Formula (I) for the treatment of a relaxin-associated disorder and a pharmaceutically acceptable carrier.

Another aspect of the invention is a method of treating a disease associated with relaxin comprising administering an effective amount of a compound of Formula (I).

Another aspect of the invention is a method of treating a cardiovascular disease comprising administering an effective amount of a compound of Formula (I) to a patient in need thereof.

Another aspect of the invention is a method of treating heart failure comprising administering an effective amount of a compound of Formula (I) to a patient in need thereof.

Another aspect of the invention is a method of treating fibrosis comprising administering a therapeutically effective amount of a compound of Formula (I) to a patient in need thereof.

Another aspect of the invention is a method of treating a disease associated with fibrosis comprising administering a therapeutically effective amount of a compound of Formula (I) to a patient in need thereof.

Another aspect of the invention is a method of treating idiopathic pulmonary fibrosis comprising administering a therapeutically effective amount of a compound of Formula (I) to a patient in need thereof.

Another aspect of the invention is a method of treating idiopathic pulmonary fibrosis comprising administering a therapeutically effective amount of a compound of Formula (I) to a patient in need thereof.

Another aspect of the invention is a method of treating or preventing kidney failure, comprising administering a therapeutically effective amount of a compound of Formula (I) to a patient in need thereof.

Another aspect of the invention is a method of improving, stabilizing or restoring renal function in a patient in need thereof, comprising administering a therapeutically effective amount of a compound of Formula (I) to the patient.

Another aspect of the invention is a method of treating a hepatic disease comprising administering a therapeutically effective amount of a compound of Formula (I) to a patient in need thereof.

Another aspect of the invention is a method of treating non-alcoholic steatohepatitis and portal hypertension comprising administering a therapeutically effective amount of a compound of Formula (I) to a patient in need thereof.

Another aspect of the invention is use of a compound of Formula (I) for prophylaxis and/or treatment of a relaxin-associated disorder.

Another aspect of the invention is a compound of Formula (I) for use in the prophylaxis and/or treatment of a relaxin-associated disorder.

Unless otherwise specified, the following terms have the stated meanings.

The term "patient" or "subject" refers to any human or non-human organism that could potentially benefit from treatment with a RXFP1 agonist as understood by practitioners in this field. Exemplary subjects include human beings of any age with risk factors for cardiovascular disease. Common risk factors include, but are not limited to, age, sex, weight, family history, sleep apnea, alcohol or tobacco use, physical inactivity, arrhythmia, or signs of insulin resistance such as acanthosis nigricans, hypertension, dyslipidemia, or polycystic ovary syndrome (PCOS).

"Treating" or "treatment" cover the treatment of a disease-state as understood by practitioners in this field and include the following: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

"Preventing" or "prevention" cover the preventive treatment (i.e., prophylaxis and/or risk reduction) of a subclinical disease-state aimed at reducing the probability of the occurrence of a clinical disease-state as understood by practitioners in this field. Patients are selected for preventative therapy based on factors that are known to increase risk of suffering a clinical disease state compared to the general population.

"Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. "Risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination with other agents to treat disorders as understood by practitioners in this field. When applied to a combination, the term refers to combined amounts of the active ingredients that result in the preventive or therapeutic effect, whether administered in combination, serially, or simultaneously.

"Disorders of the cardiovascular system" or "cardiovascular disorders" include for example the following disorders: hypertension (high blood pressure), peripheral and cardiac vascular disorders, coronary heart disease, stable and unstable angina pectoris, heart attack, myocardial insufficiency, abnormal heart rhythms (or arrhythmias), persistent ischemic dysfunction ("hibernating myocardium"), temporary postischemic dysfunction ("stunned myocardium"), heart failure, disturbances of peripheral blood flow, acute coronary syndrome, heart failure, heart muscle disease (cardiomyopathy), myocardial infarction and vascular disease (blood vessel disease).

"Heart failure" includes both acute and chronic manifestations of heart failure, as well as more specific or related types of disease, such as advanced heart failure, post-acute heart failure, cardio-renal syndrome, heart failure with impaired kidney function, chronic heart failure, chronic heart failure with mid-range ejection fraction (HFmEF), compensated heart failure, decompensated heart failure, right heart failure, left heart failure, global failure, ischemic cardiomyopathy, dilated cardiomyopathy, heart failure associated with congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, systolic heart failure, acute phases of worsening heart failure, heart failure with preserved ejection fraction (HFpEF), heart failure with reduced ejection fraction (HFrEF), chronic heart failure with reduced ejection fraction (HFrEF), chronic heart failure with preserved ejection fraction (HFpEF), post myocardial remodeling, angina, hypertension, pulmonary hypertension and pulmonary artery hypertension.

"Fibrotic disorders" encompasses diseases and disorders characterized by fibrosis, including among others the following diseases and disorders: hepatic fibrosis, cirrhosis of the liver, NASH, pulmonary fibrosis or lung fibrosis, cardiac fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

Relaxin-associated disorders include but are not limited to disorders of the cardiovascular system and fibrotic disorders.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., Remington: *The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds may be employed in combination with other suitable therapeutic agents useful in the treatment of diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The additional therapeutic agents may include ACE inhibitors, β-blockers, diuretics, mineralocorticoid receptor antagonists, ryanodine receptor modulators, SERCA2a activators, renin inhibitors, calcium channel blockers, adenosine A1 receptor agonists, partial adenosine A1 receptor, dopamine p-hydroxylase inhibitors, angiotensin II receptor antagonists, angiotensin II receptor antagonists with biased agonism for select cell signaling pathways, combinations of angiotensin II receptor antagonists and neprilysin enzyme inhibitors, neprilysin enzyme inhibitors, soluble guanylate cyclase activators, myosin ATPase activators, rho-kinase 1 inhibitors, rho-kinase 2 inhibitors, apelin receptor agonists, nitroxyl donating compounds, calcium-dependent kinase II inhibitors, antifibrotic agents, galectin-3 inhibitors, vasopressin receptor antagonists, FPR2 receptor modulators, natriuretic peptide receptor agonists, transient receptor potential vanilloid-4 channel blockers, anti-arrhythmic agents, $I_f$ "funny current" channel blockers, nitrates, digitalis compounds, inotropic agents and β-receptor agonists, cell membrane resealing agents for example Poloxamer 188, anti-hyperlipidemic agents, plasma HDL-raising agents, anti-hypercholesterolemic agents, cholesterol biosynthesis inhibitors (such as HMG CoA reductase inhibitors), LXR agonist, FXR agonist, probucol, raloxifene, nicotinic acid, niacinamide, cholesterol absorption inhibitors, bile acid sequestrants, anion exchange resins, quaternary amines, cholestyramine, colestipol, low density lipoprotein receptor inducers, clofibrate, fenofibrate, bezafibrate, ciprofibrate, gemfibrizol, vitamin B6, vitamin B12, anti-oxidant vitamins, anti-diabetes agents, platelet aggregation inhibitors, fibrinogen receptor antagonists, aspirin and fibric acid derivatives, PCSK9 inhibitors, aspirin, and P2Y12 Inhibitors such as Clopidogrel.

The additional therapeutic agents may also include nintedanib. Pirfenidone, LPA1 antagonists, LPA1 receptor antagonists, GLP1 analogs, tralokinumab (IL-13, AstraZeneca), vismodegib (hedgehog antagonist, Roche), PRM-151 (pentraxin-2, TGF beta-1, Promedior), SAR-156597 (bispecific Mab IL-4&IL-13, Sanofi), simtuzumab ((anti-lysyl oxidase-like 2 (anti-LOXL2) antibody. Gilead), CKD-942, PTL-202 (PDE inh/pentoxifylline/NAC oral control, release, Pacific Ther.), omipalisib (oral PI3K/mTOR inhibitor, GSK), IW-001 (oral sol, bovine type V collagen mod., ImmuneWorks), STX-100 (integrin alpha V/beta-6 ant, Stromedix/Biogen), Actimmune (IFN gamma), PC-SOD (midismase; inhaled, LTT Bio-Pharma/CKD Pharm), lebrikizumab (anti-IL-13 SC humanized mAb, Roche). AQX-1125 (SHIP1 activator, Aquinox), CC-539 (JNK inhibitor, Celgene), FG-3019 (FibroGen), SAR-100842 (Sanofi), and obeticholic acid (OCA or INT-747, Intercept).

The above other therapeutic agents, when employed in combination with the compounds of the present invention may be used, for example, in those amounts indicated in the *Physicians' Desk Reference*, as in the patents set out above, or as otherwise determined by practitioners in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

The compounds of the present invention are also useful as standard or reference compounds, for example as a quality standard or control, in tests or assays involving RXFP1. Such compounds may be provided in a commercial kit, for example, for use in pharmaceutical research involving RXFP1. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving RXFP1.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemical Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis,* 4th Edition. Wiley (2007)).

Abbreviations are defined as follows: “1×” for once, “2×” for twice, “3×” for thrice, “° C.” for degrees Celsius, “aq” for aqueous, “eq” or “equiv.” for equivalent or equivalents, “g” for gram or grams, “mg” for milligram or milligrams, “L” for liter or liters, “mL” for milliliter or milliliters, “L” for microliter or microliters, “N” for normal, “M” for molar, “nM” for nanomolar, “pM” for picomolar, “mol” for mole or moles, “mmol” for millimole or millimoles, “min” for minute or minutes, "h" for hour or hours, "rt" for room temperature, "RT" for retention time, "atm" for atmosphere, "psi" for pounds per square inch, "conc." for concentrate, "aq" for "aqueous", "sat." for saturated, "MW" for molecular weight, "MS" or "Mass Spec" for mass spectrometry, "ESI" for electrospray ionization mass spectroscopy, "LC-MS" for liquid chromatography mass spectrometry. "HPLC" for high pressure liquid chromatography. "RP HPLC" for reverse phase HPLC, "NMR" for nuclear magnetic resonance spectroscopy, "SFC" for super critical fluid chromatography, "[1]H" for proton. "δ" for delta. "s" for singlet, "d" for doublet, "t" for triplet, "q" for quartet, "in" for multiplet, "br" for broad, "Hz" for hertz, "MHz" for megahertz, and "α", "β", "R", "S", "E", and "Z" are stereochemical designations familiar to one skilled in the art.

| | |
|---|---|
| AcCl | acetyl chloride |
| AcOH | acetic acid |
| AIBN | azobisisobutyronitrile |
| Boc | tert-butyloxycarbonyl |
| BuLi | butyl lithium |
| DCE | dichloroethane |
| DCM | dichloromethane |
| DIEA | diispropyl ethylamine |
| DMAP | 4-dimethylamino pyridine |
| DMF | dimethylformamide |
| $Et_2O$ | diethyl ether |
| EtOAc | ethylacetate |
| EtOH | ethanol |
| HATU | (1-[Bis(dimethylamino)methylene]-1H-1,2,3-triazolo[4,5-b]pyridinium 3-oxid hexafluorophosphate) |
| IPA | isopropanol |
| i-Pr | isopropyl |
| KHMDS | potassium bis(trimethylsilyl)amide\ |
| LDA | lithium diisopropyl amide |
| MeCN | acetonitrile |
| MeOH | methanol |
| Me | methyl |
| NBS | N-bromosuccinimide |
| Pd/C | palladium on carbon |
| pTsOH | p-toluenesulfonic acid |
| PyBroP | Bromotripyrrolidinophosphonium hexafluorophosphate |
| T3P | 2,4,6-Tripropyl-1,3,5,2,4,6-trioxatriphosphorinane-2,4,6-trioxide |
| TBAF | tetra-n-butyl ammonium fluoride |
| t-Bu | tert-butyl |
| Teoc | 2-(trimethyl silyl)ethyl |
| TFA | trifluoro acetic acid |
| TFAA | trifluoro acetic anhydride |
| THF | tetrahydrofuran |
| XPhos—Pd-G2 | 2nd generation XPhos precatalyst CAS no. 1310584-14-5 |

The following methods were used in the exemplified examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water. 10% MeOH, 0.1% TFA) and Solvent B (10% water, 90% MeOH, 0.1% TFA) or with gradients of Solvent A (95% water, 5% ACN, 0.1% TFA) and Solvent B (5% water, 95% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$).

LC/MS methods employed in characterization of examples are listed below.

Method A:
- Instrument: Waters Acquity coupled with a Waters MICROMASS® ZQ Mass Spectrometer
- Linear gradient of 2 to 98% B over 1 min, with 0.5 min hold time at 98% B
- UV visualization at 220 nm
- Column: Waters BEH C18, 2.1×50 mm
- Flow rate: 0.8 mL/min (Method A)
- Mobile Phase A: 0.05% TFA, 100% water
- Mobile Phase B: 0.05% TFA, 100% acetonitrile Method B:
- Instrument: Shimadzu Prominence HPLC coupled with a Shimadzu LCMS-2020 Mass Spectrometer
- Linear gradient of 0 to 100% B over 3 min, with 0.75 min hold time at 100% B
- UV visualization at 220 nm
- Column: Waters Xbridge C18, 2.1×50 mm, 1.7 um particles
- Flow rate: 1 mL/min
- Mobile Phase A: 10 mM ammonium acetate, 95:5 water:acetonitrile
- Mobile Phase B: 10 mM ammonium acetate, 5:95 water:acetonitrile Method C:
- Instrument: Shimadzu Prominence HPLC coupled with a Shimadzu LCMS-2020 Mass Spectrometer
- Linear gradient of 0 to 100% B over 3 min, with 0.75 min hold time at 100% B
- UV visualization at 220 nm
- Column: Waters Xbridge C18, 2.1×50 mm, 1.7 um particles
- Flow rate: 1 mL/min
- Mobile Phase A: 0.1% TFA, 95:5 water:acetonitrile
- Mobile Phase B: 0.1% TFA, 5:95 water:acetonitrile Method D:
- Instrument: Waters Acquity coupled with a Waters MICROMASS® ZQ Mass Spectrometer
- Linear gradient of 10% B to 98% B over 1 min, with 0.5 min hold time at 98% B
- UV visualization at 220 nm
- Column: Waters Acquity GEN C18, 2.1×50 mm, 1.7 um particles
- Flow rate: 1 mL/min
- Mobile Phase A: 0.05% TFA, 100% water
- Mobile Phase B: 0.05% TFA, 100% acetonitrile Method E:
- Instrument: Agilent 1290 infinity II with G6135B Mass spectrometer
- Linear gradient of 0% B to 100% B over 3 mins
- UV visualization at 220 nm
- Column: Xbridge BEH XP C18 50×2.1 mm, 2.5 mM
- Flow rate: 1.1 mL/min at 50° C.
- Mobile Phase A: 10 mM $NH_4OAc$ in Water:ACN (95:05)
- Mobile Phase B: 10 mM $NH_4OAc$ in Water:ACN (05:95)

Method F:
- Instrument: Agilent 1290 infinity II with G6135B Mass spectrometer
- Linear gradient of 0% B to 100% B over 3 mins
- UV visualization at 220 nm
- Column: Xbridge BEH XP C18 50×2.1 mm, 2.5 mM
- Flow rate: 1.1 mL/min at 50° C.
- Mobile Phase A: 0.1% TFA in Water:ACN (95:05)
- Mobile Phase B: 0.1% TFA in Water:ACN (05:95)

NMR Employed in Characterization of Examples. $^1H$ NMR spectra were obtained with Bruker or JEOL® Fourier transform spectrometers operating at frequencies as follows: $^1H$ NMR: 400 MHz (Bruker or JEOL®) or 500 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1H$ NMR spectra appear at 2.51 ppm for DMSO-$d_6$, 3.30 ppm for $CD_3OD$, 1.94 ppm for $CD_3CN$, and 7.24 ppm for $CDCl_3$.

Syntheses of key norbornyl intermediates are outlined in Schemes I-V. Norbornyl intermediates can be made with isopropylidene bridgehead substitution as described in Scheme I, starting from I-1. Diels-Alder cyclization with maleic anhydride furnished compound 1-2, which was reduced and deprotected to yield I-3. Curtius reaction with DPPA on the free acid in the presence of trimethylsilylethanol produced 1-4. The trimethylsilylcarbamate was cleaved with TFA and the amine reprotected as the trifluoroacetamide 1-5. The methyl ester was converted to the amide via treatment with 4-fluoro-3-trifluoromethylaniline and trimethyl aluminum to furnish I-6. Deprotection of the trifluoroacetamide using $K_2CO_3$ and MeOH produced amine 1-7.

Scheme I

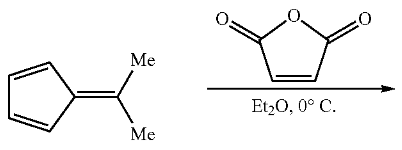

I-1

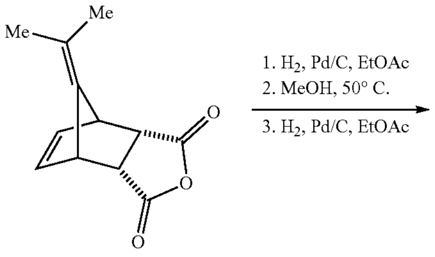

I-2

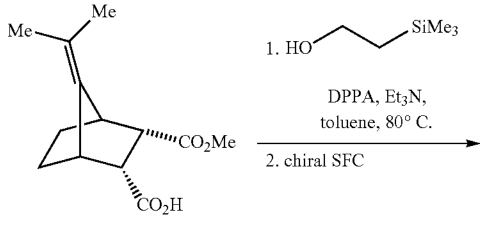

I-3

-continued

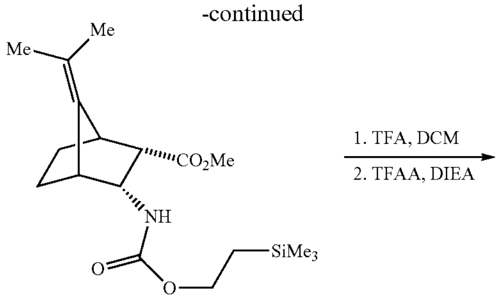

I-4
chiral

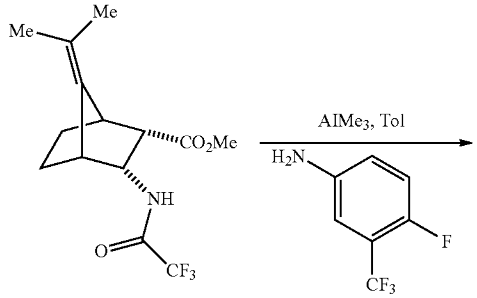

I-5

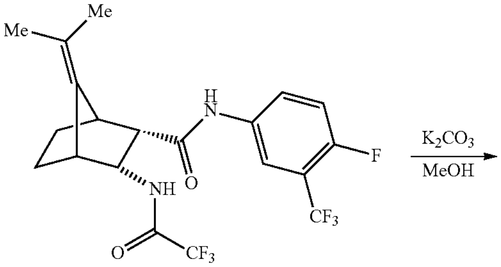

I-6

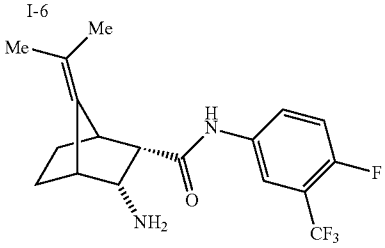

I-7

Intermediate I-2: At 0° C., into the reaction vessel was added $Et_2O$ (100 mL). 5-(propan-2-ylidene)cyclopenta-1,3-diene (10 g, 94 mmol), and furan-2,5-dione (10 g, 100 mmol). The reaction mixture was stirred at 0° C. for 18 h, concentrated under reduced pressure and purified via silica gel chromatography to provide 1-2 (3.74 g, 18.3 mmol, 19.0% yield). Intermediate I-2 is a known compound; please see: PCT Int. Appl., 2011163502, 29 Dec. 2011.

Intermediate I-3: Into the reaction vessel was added 1-2 (2.74 g, 13.4 mmol), EtOAc (100 mL), pyridine (0.540 mL, 6.71 mmol), and Pd/C (70 mg. 0.070 mmol). The reaction mixture was stirred at 23° C. under 1 atm H2 (H2 balloon) for 60 min filtered through Celite, and concentrated under reduced pressure. The residue was dissolved in MeOH (50 mL) and heated at 50° C. for 12 h. The solution was concentrated under reduced pressure (azeotroped with toluene 3x15 mL) to produce 1-3 (3.21 g, 13.5 mmol, 100% yield) that was used without further purification.

Intermediate I-4: Into the reaction vessel was added I-3 (3.21 g, 13.5 mmol), $Et_3N$ (3.38 mL, 24.2 mmol), toluene (75 mL), and diphenylphosphoryl azide (4.35 mL, 20.2 mmol). The reaction mixture was stirred at 23° C. for 1 h and subsequently heated at 85° C. for 30 min. 2-(trimethylsilyl) ethanol (4.83 mL, 33.7 mmol) was added to the reaction mixture and, after stirring at 85° C. for 66 h, the reaction mixture was allowed to cool to 23° C. and purified via silica gel chromatography to provide racemic 1-4 (3.71 g, 10.5 mmol, 78% yield) LC-MS RT=1.25 min; (M+H)=354.1. Method A. Racemic 1-4 was separated into individual enantiomers using chiral SFC. Preparative chromatographic conditions: Instrument: Thar 350 SFC; Column: Whelko-RR, 5×50 cm, 10 micron; Mobile phase: 13% IPA/87% $CO_2$; Flow conditions: 300 mL/min, 100 Bar, 35° C.; Detector wavelength: 220 nm; Injections details: 4 injections of 3.5 mL of 59 g/490 mL MeOH:DCM (4:1) 120 mg/mL in IPA. Analytical chromatographic conditions: Instrument: Thar analytical SFC; Column: Whelko-RR (0.46×25 cm, 5 micron; Mobile phase: 5% IPA/95% $CO_2$; Flow conditions: 3 mL/min, 140 Bar. 40° C.; Detector wavelength: 200-400 nm UV; RT=3.50 Peak #1, 4.42 Peak #2. Intermediate I-4 product Peak #1 was collected and carried forward to produce chiral 1-5.

Intermediate I-5: Peak #1 of intermediate 1-4 (2.87 g, 8.12 mmol) was dissolved in 10:1 DCM/TFA and stirred at rt for 72 h. The reaction mixture was concentrated under reduced pressure to generate (1R,2S,3R,4R)-methyl 3-amino-7-(propan-2-ylidene)bicyclo[2.2.1]heptane-2-carboxylate (1.699 g, 8.120 mmol, 100% yield) which was used without further purification. To (1R,2S,3R,4R)-methyl 3-amino-7-(propan-2-ylidene)bicyclo[2.2.1]heptane-2-carboxylate (1.7 g, 8.1 mmol) was added DCM (41 mL) and the flask was cooled to 0° C. via an ice bath. TFAA (1.26 mL, 8.90 mmol) and DIEA (5.7 mL, 33 mmol) were added. The reaction mixture was allowed to warm to 23° C. and stirred for 30 min. Saturated $NaHCO_3$ (50 mL) was added to the reaction mixture and the solution extracted with EtOAc (3×50 mL). The combined organic portions were dried over $Na_2SO_4$ filtered and concentrated under reduced pressure to afford 1-5 (2.48 g, 8.12 mmol, 100% yield) that was used without further purification. LC-MS RT=1.11 min; MS (ESI) m/z=306.1 $(M+H)^+$; Method A.

Intermediate I-6: To a solution of intermediate 1-5 (2.7 g, 8.8 mmol) in toluene (88 ml) was added trimethylaluminum (26.5 mmol) premixed with 4-fluoro-3(trifluoromethyl)aniline (29.2 mmol) as a solution in toluene (0.275 M in amine, 0.25 M in trimethylaluminum). The reaction mixture was stirred at 60° C. for 30 min. On cooling to rt, the reaction mixture was diluted with EtOAc (100 mL) and sat. Rochelle's salt (100 mL) added. The aqueous portion was extracted with EtOAc (3×75 mL). The combined organic portion was dried over $Na_2SO_4$, filtered, concentrated under reduced pressure, and subjected to silica gel chromatography purification and the residue further purified by preparative reverse phase HPLC to yield (1R,2S,3R,4R)—N-(4-fluoro-3-(trifluoromethyl)phenyl)-7-(propan-2-ylidene)-3-(2,2,2-trifluoroacetamido)bicyclo[2.2.1]heptane-2-carboxamide I-6 (2.5 g, 5.5 mmol, 63% yield) as a yellow foam. LC-MS RT=1.20 min; MS (ESI) m/z=453.0 (M+H); Method A.

Intermediate I-7: Intermediate I-6 (133 mg, 0.290 mmol) was dissolved in water (2.9 mL) and MeOH (2.9 mL), then $K_2CO_3$ (2.03 g, 1.47 mmol) was added. The reaction mixture was stirred at 40° C. for 4 h, then partitioned between water (5 mL) and extracted with EtOAc (3×10 mL). The combined organic extracts were dried over $Na_2SO_4$ filtered and concentrated under reduced pressure to afford I-7 (105 mg, 0.290 mmol, 100% yield) that was used without further purification. LC-MS RT=0.82 min; MS (ESI) m/z=357.1 $(M+H)^+$; Method A.

Scheme Ia

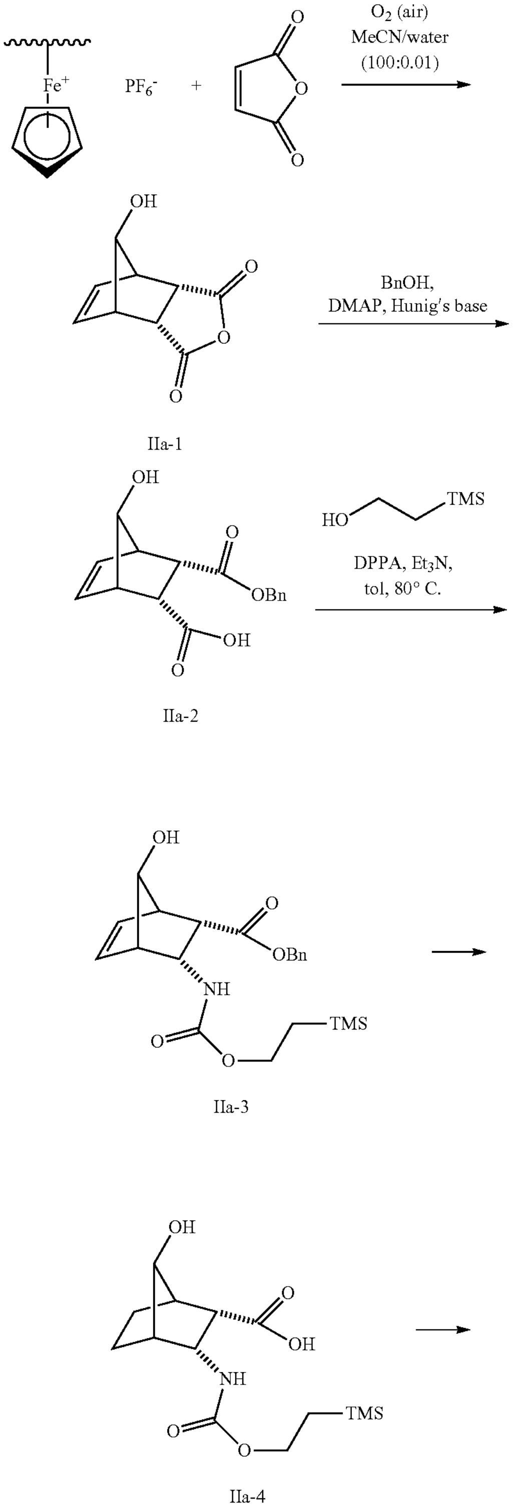

IIa-1

IIa-2

IIa-3

IIa-4

-continued

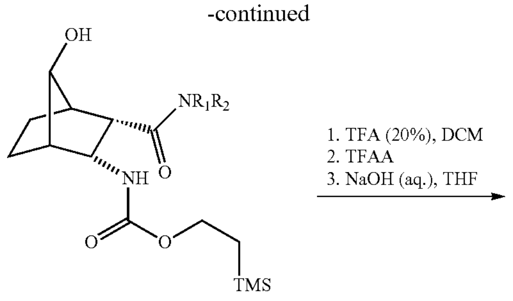

IIa-5

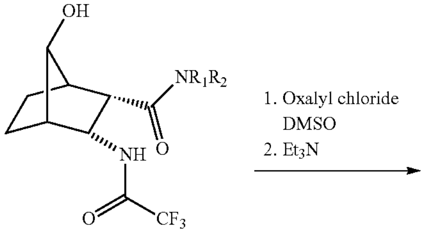

IIa-6

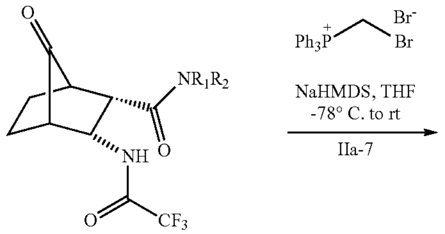

IIa-7

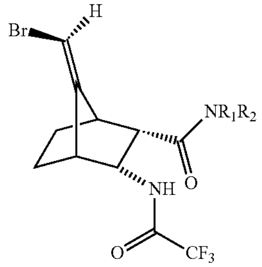

IIa-8
Major

+

-continued

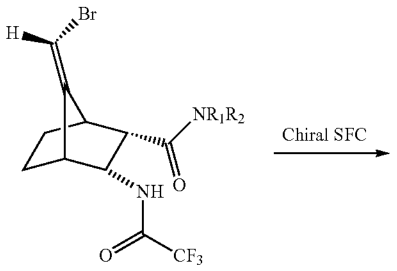

Minor

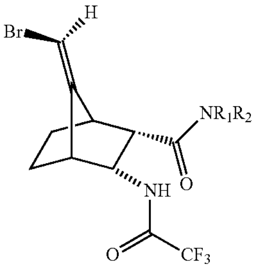

IIa-8 (-)
Major

The norbornyl intermediate IIa-8 could also be prepared by the general route shown in Scheme Ia from furan-2,5-dione and ferrocenium hexafluorophosphate. Diels Alder condensation, followed by hydrolysis to IIa-2, Curtius rearrangement to the intermediate amine which was reduced under hydrogenation conditions and subsequently protected to generate intermediate IIa-3. Cleavage of the benzyl ester and cross coupling to $NHR_1R_2$ generated intermediates with the general structure IIa-5. Conversion of the C7 hydroxy group to the ketone followed by Wittig olefination generated major isomer intermediate IIa-8. The major isomer was separated from the minor isomer by chromatography and the racemate separated into enantiopure IIa-8 (−).

Scheme II shows how intermediate I-6 was converted to an olefinic bromide intermediate that allows for cross-coupling reactions at the C-7 methylidene.

Scheme II

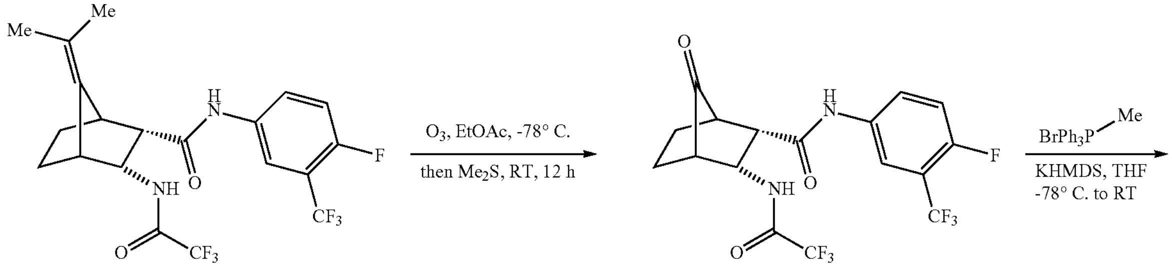

I-6 II-1

-continued

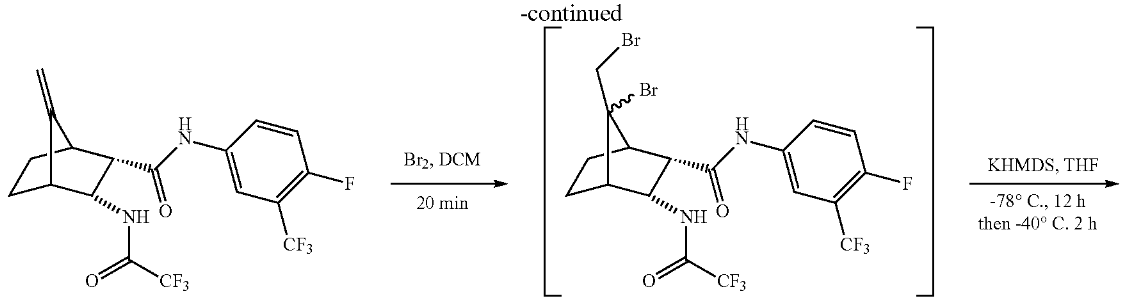

II-2

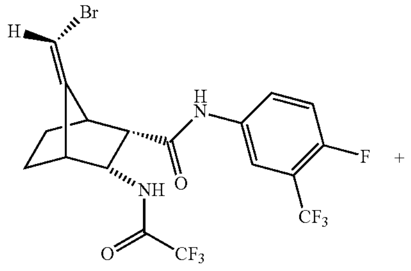

II-3

(peak 1, silica gel chrom.)

+

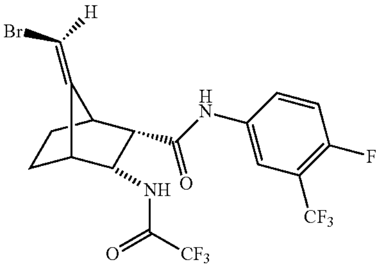

II-4

(peak 2, silica gel chrom.)

chiral SFC

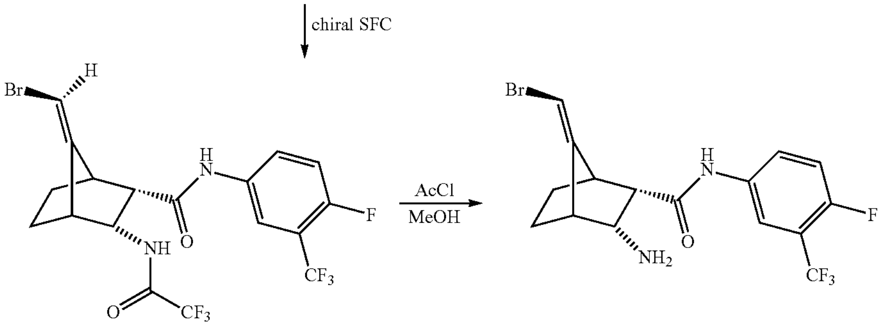

II-4
chiral
peak 1

II-5

Intermediate II-1 Into the reaction vessel was added intermediate 1-6 (110 mg, 0.243 mmol) and EtOAc (2 mL). The reaction mixture was cooled to −78° C. and $O_3$ was bubbled through the solution until the solution became pale purple/blue. $N_2$ was subsequently bubbled through the solution at −78° C. to remove excess 03 (solution became colorless). Dimethyl sulfide (0.43 mL, 4.8 mmol) was subsequently added at −78° C. and the reaction mixture was allowed to warm to rt and stirred at rt for 12 h. After concentrating under reduced pressure, the residue was dissolved in EtOAc and filtered through silica gel to generate (1R,2S,3R,4S)—N-(4-fluoro-3-(trifluoromethyl)phenyl)-7-oxo-3-(2,2,2-trifluoroacetamido)bicyclo[2.2.1]heptane-2-carboxamide after removal of solvent under reduced pressure, (11-1, 101 mg, 0.237 mmol, 97.0% yield). $^1$H NMR (500 MHz, $CDCl_3$) S 9.61 (br d, J=6.3 Hz, 1H), 7.76 (dd, J=5.9, 2.6 Hz, 1H), 7.71 (dt, J=8.9, 3.4 Hz, 1H), 7.66 (s, 1H), 7.23 (t, J=9.4 Hz, 1H), 4.70 (dt, J=10.3, 5.3 Hz, 1H), 3.33 (dd, J=10.5, 4.4 Hz, 1H), 2.54 (t, J=4.3 Hz, 1H), 2.42 (t, J=4.1 Hz, 1H), 2.20-2.10 (m, 1H), 2.06-1.99 (m, 1H), 1.96-1.81 (m, 2H).

Intermediate 11-2: Into the reaction vessel was added bromo(methyl)triphenylphosphorane (419 mg, 1.17 mmol) (fine powder by grinding the commercial material) and THF (7 mL). The reaction mixture was cooled to −78° C. and KHMDS (1.2 mL, 1.2 mmol) was added. The reaction mixture was allowed to stir vigorously at −78° C. for 30 min and II-1 (100 mg, 0.24 mmol) was added at −78° C. After stirring at −78° C. for a further 10 min, the reaction mixture was allowed to warm to 23° C. and stirred for a further 1.5 h. The reaction mixture was cooled to −40° C. and quenched by the addition of sat. $NaHCO_3$. The resulting solution was extracted with EtOAc. The combined organic portion was dried over $Na_2SO_4$, filtered, concentrated under reduced pressure, and purified via silica gel chromatography to produce II-2 (71 mg, 0.17 mmol, 71% yield). LCMS RT=1.16 min; (M+H)=425.0; Method A.

Intermediates 11-3 and H-4: Into the reaction vessel was added 11-2 (71 mg, 0.17 mmol), DCM (3 mL), and $Br_2$ (0.03 mL, 0.6 mmol). The reaction mixture was stirred at 23° C. for 20 min and concentrated under reduced pressure utilizing a trap with sat. $Na_2S_2O_3$ to quench excess $Br_2$. The resulting dibromide was dissolved in THF (3 mL). After cooling to −78° C., KHMDS (1.0 mL, 1.0 mmol) was added. The reaction mixture was kept at −78° C. for 12 h and −40° C.

for 2 h, quenched by the addition of sat. $NaHCO_3$ at −40° C., and the resulting solution extracted with EtOAc. The organic phase was collected, dried over $Na_2SO_4$, filtered, concentrated under reduced pressure, and purified via silica gel chromatography to produce 11-4 (27 mg, 0.050 mmol, 32% yield) (peak2). LCMS RT=1.19 min; (M+H)=504.9; Method A. and the corresponding E-isomer II-3 (28 mg, 0.06 mmol, 33% yield) (peak 1).

Racemic 1-4 (4 grams) was produced as outlined above and separated into individual enantiomers using chiral SFC. Preparative chromatographic conditions: Instrument: Thar 350 SFC; Column: Chiralcel OD-H, 5×50 cm, 5 micron; Mobile phase: 20% MeOH/80% $CO_2$; Flow conditions: 340 mL/min, 100 Bar, 35° C.; Detector wavelength: 220 nm; Injections details: 3.75 mL of 30 mg/mL in MeOH. Peak #1 RT=7.81 min, Peak #2 RT=10.97 min. Peak #1 of 11-4 (1.9 grams) was collected and carried forward to produce chiral 11-5.

Intermediate 11-5: Into the reaction was added MeOH (3 mL) and AcCl (0.3 mL, 4.2 mmol). After stirring for 5 min, chiral Peak #1 II-4 (75 mg, 0.15 mmol) was added and the reaction mixture was stirred at 40° C. for 48 h. The reaction mixture was concentrated under reduced pressure produced 11-5 (67 mg, 0.16 mmol, 100%) that was used without further purification. LC-MS RT=0.78 min; (M+H)=408.9; Method A.

Scheme III

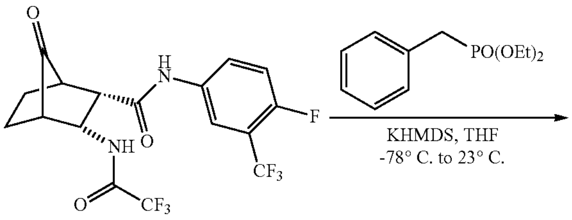

II-1

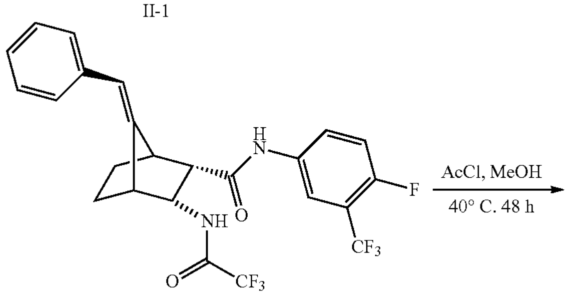

III-1
separate olefin isomers
silica gel chrom.

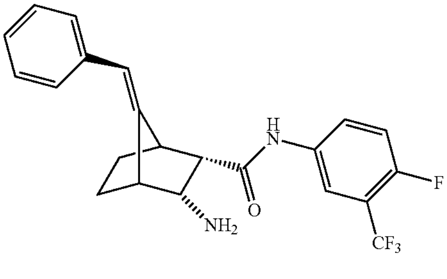

III-2

Intermediate III-1: In to the reaction vessel was added diethyl benzylphosphonate (375 mg, 1.64 mmol) and THF (10 mL). The reaction mixture was cooled to −78° C. and KHMDS (1.6 mL, 1.6 mmol) was added. This reaction mixture was stirred at −78° C. for 10 min and intermediate II-1 (140 mg, 0.328 mmol) was added. After 20 min, the reaction mixture was allowed to warm to rt and stirred at rt for 2 h. The reaction mixture was quenched by the addition of sat $NaHCO_3$ and the solution extracted with EtOAc. The combined organic portion was dried over $Na_2SO_4$, filtered, concentrated, and subjected to silica gel chromatography purification to the E-isomer byproduct (111 mg, 0.222 mmol, 67.5% yield) and (1R,2S,3R,4R,Z)-7-benzylidene-N-(4-fluoro-3-(trifluoromethyl)phenyl)-3-(2,2,2-trifluoroacetamido)bicyclo[2.2.1]heptane-2-carboxamide (III-1, 49 mg, 0.098 mmol, 30% yield). RT=1.23 min; MS (ESI) m/z=501.1 $(M+H)^+$; Method A.

Intermediate III-2: To a vial containing MeOH (3 mL) cooled to 0° C. (ice/water bath) was added acetyl chloride (0.3 mL, 4 mmol) dropwise. The resulting solution was stirred at rt for 10 min, then was added to III-1 (94 mg, 0.19 mmol). The reaction mixture was stirred at 40° C. for 48 h and concentration under reduced pressure afforded (1R,2S,3R,4R)-3-amino-7-((Z)-benzylidene)-N-(4-fluoro-3-(trifluoromethyl)phenyl)bicyclo[2.2.1]heptane-2-carboxamide (III-2, 73 mg. 0.18 mmol, 96% yield). RT=0.87 min; MS (EST) m/z=405.1 $(M+H)^+$; Method A which was used without further purification.

Scheme IV demonstrates a general route to install C7 bridgehead functionality in similar manner as Scheme II, for example, but not limited to, cyclopropyl, cyclobutyl, and nBu.

Scheme IV

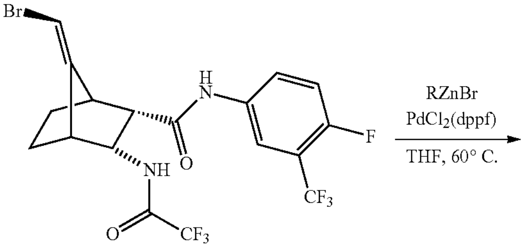

II-4

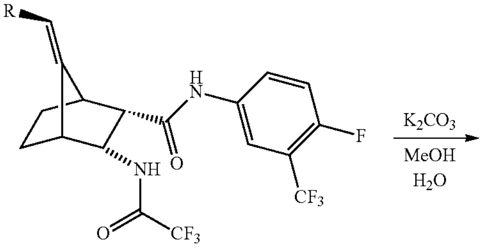

IV-1a, R = $^{cy}Pr$
IV-1b, R = $^{cy}Bu$
IV-1c, R = nBu

-continued

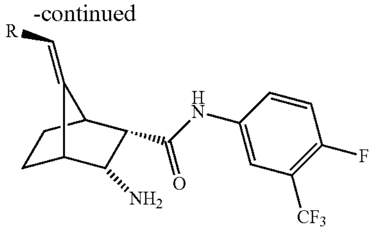

IV-2a, R = $^{cy}$Pr
IV-2b, R = $^{cy}$Bu
IV-2c, R = nBu

Intermediate IV-1a: A solution of 11-4 (1.00 g, 1.98 mmol) in THF (9.9 mL) was treated with $PdCl_2$(dppf) (0.073 g, 0.099 mmol), under $N_2$, then cyclopropylzinc(II) bromide (15.9 mL, 7.95 mmol) was added and the reaction mixture heated to 60° C. for 2 h. The cooled reaction mixture was extracted from brine with EtOAc, and the combined organic portion concentrated under reduced pressure. The residue was purified by silica gel chromatograph to furnish (1R,2S, 3R,4R,Z)-7-(cyclopropylmethylene)-N-(4-fluoro-3-(trifluoromethyl)phenyl)-3-(2,2,2-trifluoroacetamido)bicyclo [2.2.1]heptane-2-carboxamide (IV-1a, 646 mg, 1.39 mmol, 70.0% yield). LC-MS RT=1.07 min, MS (EST) m/z=492.1 $(M+H)^+$; Method A.

Intermediate IV-2: A solution of IV-1a (646 mg, 1.39 mmol) in MeOH (9.3 mL) was treated with $K_2CO_3$ (961 mg, 6.96 mmol) in water (4.6 mL) and the reaction mixture was stirred for 18 h. The reaction mixture was extracted from phosphate buffer with EtOAc. The organic layer was concentrated to furnish (1R,2S,3R,4R,Z)-3-amino-7-(cyclopropylmethylene)-N-(4-fluoro-3-(trifluoromethyl)phenyl)bicyclo[2.2.1]heptane-2-carboxamide which was used without further purification (IV-2a, 512 mg, 1.39 mmol, 100% yield). RT=0.84 min; MS (ESI) m/z=369.1 $(M+H)^+$; Method A.

Intermediates IV-1b,c and IV-2b,c were prepared analogously from commercially available organozinc reagents.

Scheme V

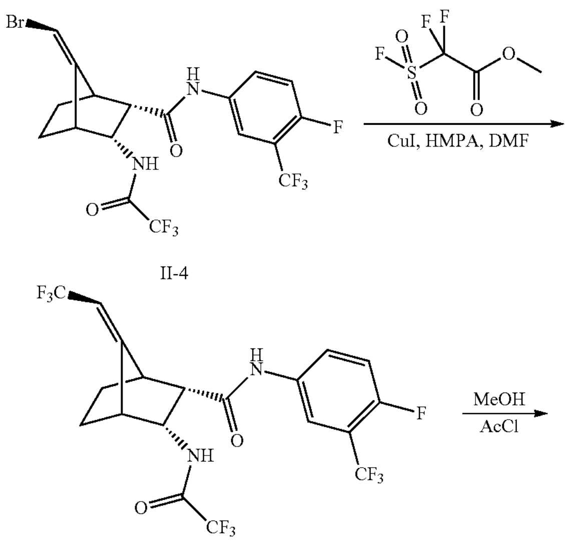

II-4

V-1

-continued

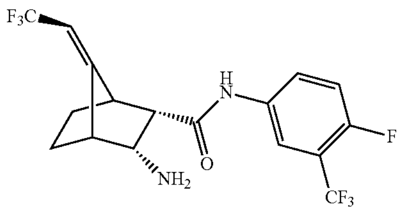

V-2

Intermediate V-1: Intermediate V-1 was prepared from 11-4. To a 250 mL round bottom flask charged with methyl 2,2-difluoro-2-(fluorosulfonyl)acetate (2.5 mL, 20 mmol) in anhydrous DMF (50 mL) was added dropwise via dropping funnel to a suspension of 11-4 and Cui (2.3 g, 12 mmol) in anhydrous DMF (100 mL) and HMPA (8.0 mL, 19 mmol) and the reaction mixture heated at 75° C. under an inert nitrogen atmosphere for 16 h. The cooled reaction mixture was filtered and purified by silica gel chromatography to produce V-1 (3.0 g, 6.1 mmol, 77% yield). 1H NMR (500 MHz, $CDCl_3$) S 9.38 (br d, J=6.1 Hz, 1H), 7.77-7.69 (m, 2H), 7.46 (s, 1H), 7.24 (t, J=9.1 Hz, 1H), 5.62 (q, J=7.2 Hz, 1H), 4.50 (dt, J=10.5, 5.3 Hz, 1H), 3.50-3.42 (m, 1H), 3.13-3.04 (m, 1H), 2.89 (t, J=4.0 Hz, 1H), 2.02-1.90 (m, 2H), 1.76-1.60 (m, 2H).

Intermediate V-2: Intermediate V-2 was prepared from V-1. MeOH (1.5 mL) and acetyl chloride (2.1 mmol) were charged into a 2 dram vial and stirred at 23° C. for 5 min. V-1 was added to the reaction vial and the contents heated at 40° C. for 24 h. Concentration with a stream of nitrogen gave V-2 as the HCl salt which was used without further purification. LC-MS RT=0.75 min; MS (ESI) m/z=397.1 $(M+H)^+$; Method A.

Example 2

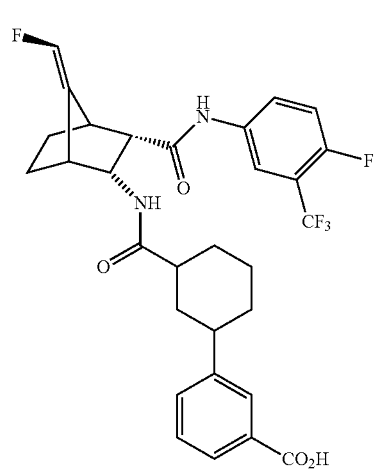

Intermediate VI-1

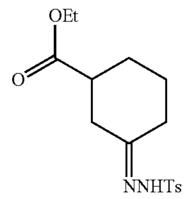

A slurry of 4-methoxybenzenesulfonohydrazide (595 mg, 2.94 mmol), ethyl 3-oxocyclohexane-1-carboxylate (500 mg, 2.94 mmol) in dioxane (14.7 mL) was heated at 80° C. The reaction mixture was concentrated under reduced pressure and the residue purified by silica gel chromatography to furnish ethyl (Z)-3-(2-((4-methoxyphenyl)sulfonyl)hydrazineylidene) cyclohexane-1-carboxylate (VI-1, 904 mg, 2.55 mmol, 87% yield) which was used without further purification.

Intermediate VI-2

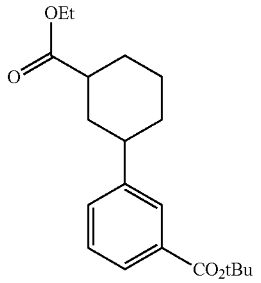

A slurry of (3-(tert-butoxycarbonyl)phenyl)boronic acid (0.329 g, 1.48 mmol), intermediate VI-1 (0.350 g, 0.988 mmol), $Cs_2CO_3$ (0.804 g, 2.47 mmol) in dioxane (4.9 mL) was heated at 110° C. for 18 h. The reaction mixture was partitioned between water and EtOAc. The organic layer was concentrated under reduced pressure and the residue purified by silica gel chromatography to furnish tert-butyl 3-(3-(ethoxycarbonyl)cyclohexyl)benzoate (VI-2, 192 mg, 0.578 mmol, 58.5% yield). MS (ESI) m/z=277 (M+H−tBu)+

Intermediate VI-3

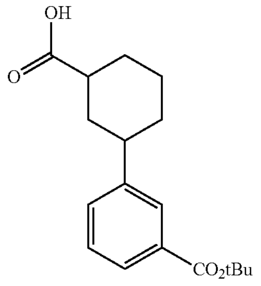 [SMILES: CC(C)(C)OC(=O)c1cccc(C2CCCC(C(=O)O)C2)c1]

A solution of intermediate VI-2 (140 mg, 0.421 mmol) in THF (3.5 mL) was treated with LiOH (20 mg, 0.84 mmol) in water (0.7 mL). The reaction mixture was adjusted to pH 3 by the addition of dilute HCl (1N), filtered through celite, and concentrated under reduced pressure to furnish 3-(3-(tert-butoxycarbonyl)phenyl)cyclohexane-1-carboxylic acid (VI-3, 128 mg. 0.421 mmol, 100% yield) which was used without further purification. MS (ESI) m/z=249 (M+H−tBu)+

Intermediate 1-1

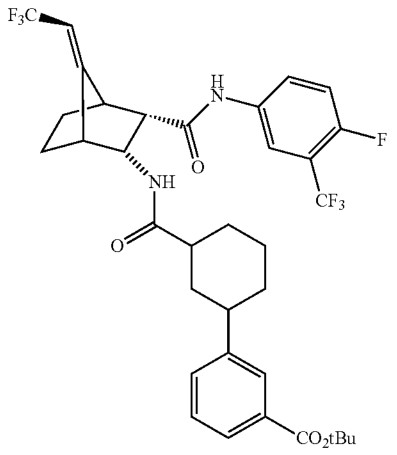

To intermediate VI-3 (121 mg, 0.280 mmol) dissolved in MeCN (2.8 mL) was added Hunig's Base (0.25 mL, 1.4 mmol), intermediate V-2 (128 mg, 0.421 mmol), and HATU (128 mg, 0.336 mmol) and the mixture was stirred for 18 h. The reaction mixture was extracted from water with EtOAc. The organic layer was concentrated under reduced pressure and the residue purified by silica gel chromatography to furnish tert-butyl 3-(3-(((I R2R,3S,4R,Z)-3-((4-fluoro-3-(trifluoromethyl)phenyl)carbamoyl)-7-(2,2,2-trifluoroethylidene)bicyclo[2.2.1]heptan-2-yl)carbamoyl)cyclohexyl) benzoate (2-1, 130 mg, 0.190 mmol, 67.9% yield). MS (ESI) m/z=627 (M+H−tBu)+

Example 1

A solution of 1-1 (130 mg, 0.190 mmol) in DCM (0.7 mL) was treated with TFA (0.3 mL). After 2 h, the reaction mixture was concentrated under reduced pressure and the residue purified by reverse phase HPLC to generate 3-(3-(((1R2R,3S,4R,Z)-3-((4-fluoro-3-(trifluoromethyl)phenyl) carbamoyl)-7-(2,2,2-trifluoroethylidene)bicyclo[2.2.1]heptan-2-yl)carbamoyl)cyclohexyl)benzoic acid as a mixture of four stereoisomers. The diastereomers were partially resolved by SFC (Chiral AS, 30×250 mm, 5 micron, 100 mL/min, 40° C., 120 bar, 85% $CO_2$/15% MeOH w/0.1% DEA (isocratic)).

Example 1: Peak 1 (single isomer, RT=4.49 min); 3-(3-(((1R,2R,3S,4R,Z)-3-((4-fluoro-3-(trifluoromethyl)phenyl) carbamoyl)-7-(2,2,2-trifluoroethylidene)bicyclo[2.2.1]heptan-2-yl)carbamoyl)cyclohexyl)benzoic acid (1.1 mg, 1.6 μmol, 0.87% yield). $^1$H NMR (500 MHz, DMSO-d6) δ 10.56 (s, 1H), 8.38 (br d, J=7.2 Hz. 1H), 8.16-8.05 (m, 1H), 7.82-7.71 (m, 3H), 7.56-7.37 (m, 3H), 5.90 (br d, J=8.1 Hz, 1H), 4.42-4.35 (m, 1H), 3.17 (br dd, J=10.4, 4.3 Hz, 1H), 3.09 (br d, J=4.6 Hz, 1H), 2.99-2.87 (m, 2H), 2.69 (br s, 1H), 2.15-1.93 (m, 4H), 1.89-1.80 (m, 1H). 1.74-1.60 (m, 2H), 1.55-1.40 (m, 6H). LC-MS RT 2.02 min; MS (ESI) m/z=627.14 (M+H)+; Method C.

Example 2 Peak 2 (single isomer, RT=6.33 min) 3-(3-(((1R,2R,3S,4R,Z)-3-((4-fluoro-3-(trifluoromethyl)phenyl) carbamoyl)-7-(2,2,2-trifluoroethylidene)bicyclo[2.2.1]heptan-2-yl)carbamoyl)cyclohexyl)benzoic acid (7.7 mg, 0.012 mmol, 6.2% yield). $^1$H NMR (500 MHz, DMSO-d6) δ 10.47 (s, 1H), 8.19 (br d, J=8.0 Hz, 1H). 8.15-8.08 (m, 1H), 7.81-7.67 (m, 3H), 7.53-7.35 (m, 3H), 5.85 (q, J=7.6 Hz, 1H), 4.36 (br s, 1H), 3.19-3.06 (m, 1H), 3.01-2.86 (m. 2H), 2.64 (br s, 1H). 2.47-2.36 (m, 1H), 2.20-1.98 (m, 2H), 1.87-1.61 (m, 4H), 1.53-1.16 (m, 7H). LC-MS RT 2.40 min; MS (ESI) m/z=627.17 (M+H)+; Method C.

Example 3

Peak 3 (mixture of two diastereomers, RT=17.34 min) 3-(3-(((1R,2R,3S,4R,Z)-3-((4-fluoro-3-(trifluoromethyl) phenyl)carbamoyl)-7-(2,2,2-trifluoroethylidene)bicyclo [2.2.1]heptan-2-yl)carbamoyl)cyclohexyl)benzoic acid (13.6 mg, 0.021 mmol, 11.2% yield). $^1$H NMR (500 MHz, DMSO-d6) δ 10.34 (br s, 1H), 8.15 (br s, 1H), 7.99 (br d, J=2.1 Hz, 1H), 7.79-7.57 (m, 3H), 7.37-7.18 (m, 3H), 5.88-5.79 (m, 1H), 4.46-4.35 (m, 1H), 3.08 (br d, J=10.4 Hz, 1H). 3.01-2.93 (m, 1H), 2.89 (br s, 1H), 2.49-2.38 (m, 2H), 2.26-1.99 (m, 2H), 1.87-1.57 (m, 4H), 1.53-1.18 (m, 7H). LC-MS RT 2.42 min; MS (ESI) m/z=627.17 (M+H)+; Method C.

Example 4

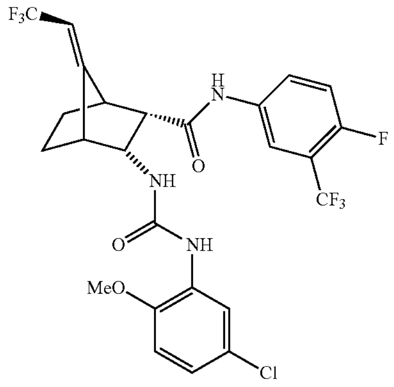

A solution of intermediate V-2 (10 mg. 0.025 mmol) in MeCN (1 mL) was treated with Hunig's Base (5 μL, 0.03 mmol) and 4-chloro-2-isocyanato-1-methoxybenzene (6.0 mg, 0.033 mmol) and BOP reagent and the reaction mixture was allowed to stir at rt for 18 h. The reaction mixture was concentrated under reduced pressure and the residue purified by reverse phase HPLC to furnish (1R,2S,3R,4R,Z)-3-(3-(5-chloro-2-methoxyphenyl)ureido)-N-(4-fluoro-3-(trifluoromethyl)phenyl)-7-(2,2,2-trifluoroethylidene)bicyclo [2.2.1]heptane-2-carboxamide (5, 5.6 mg, 8.7 μmol, 34% yield). $^1$H NMR (500 MHz, DMSO-d6) δ 10.32 (s, 1H), 8.60 (s, 1H), 8.12 (br d, J=4.6 Hz, 1H), 8.05 (d, J=1.8 Hz, 1H), 7.70-7.61 (m, 1H), 7.52-7.35 (m, 2H), 6.95-6.80 (m, 2H), 5.87 (br d, J=7.9 Hz, 1H), 4.52-4.39 (m, 1H), 3.80 (s, 3H), 3.21-3.10 (m, 1H), 3.01-2.84 (m, 2H), 2.37 (br s, 1H), 2.05 (br d, J=16.8 Hz, 1H), 1.50 (br t, J=11.9 Hz. 2H). LC-MS RT 2.52 min; MS (ESI) m/z=580.11 (M+H)+; Method C.

Example 12

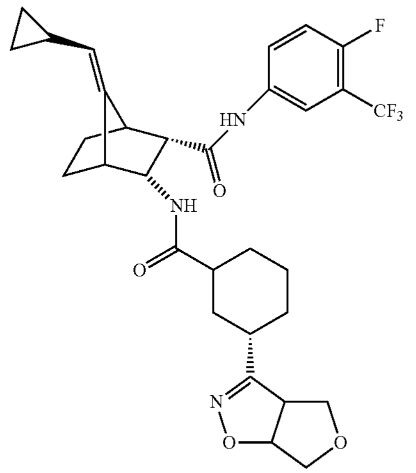

Intermediate 12-1

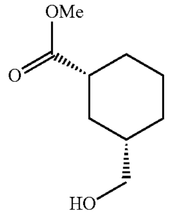 [SMILES: COC(=O)[C@@H]1CCC[C@H](CO)C1]

A solution of (1S,3R)-3-(methoxycarbonyl)cyclohexane-1-carboxylic acid (0.200 g, 1.07 mmol) in THF (3.6 mL) was treated with borane tetrahydrofuran complex (1.6 mL, 1.6 mmol) at 0° C. The reaction mixture was quenched with $NH_4C_1$ solution and extracted with EtOAc. The organic portion was concentrated under reduced pressure and the residue used without further manipulation as methyl (1R, 3S)-3-(hydroxymethyl)cyclohexane-1-carboxylate (0.185 g, 1.07 mmol, 100% yield). LC-MS (M+H)=173.1; HPLC RT=0.91 min; Method A Intermediate 12-2

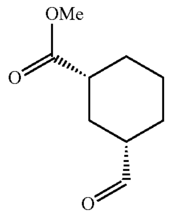 [SMILES: COC(=O)[C@@H]1CCC[C@H](C=O)C1]

A solution of oxalyl chloride (0.45 mL, 5.1 mmol) dissolved in 1 mL DCM was treated with DMSO (0.72 mL, 10. mmol) in 1 mL DCM at −78° C. After 15 min the reaction mixture was treated with 12-1 (175 mg, 1.02 mmol) dissolved in 3 mL DCM. After 30 min, the resulting solution was treated with TEA (2.1 mL 15 mmol) and allowed to slowly warn to rt. 1 N HCl was added to the reaction mixture and the solution extracted with DCM. The organic portion was concentrated under reduced pressure and the residue used without further manipulation as methyl (1R,3S)-3-formylcyclohexane-1-carboxylate (173 mg, 1.02 mmol, 100% yield). $^1$H NMR (500 MHz, $CDCl_3$) S 9.64 (d, J=1.2 Hz, 1H), 3.71 (s, 3H), 2.62-2.55 (m, 4H), 2.06-1.94 (m, 4H), 1.41-1.36 (m, 2H)

Intermediate 12-3

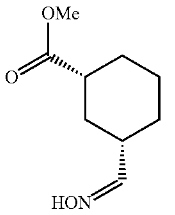

A solution of 12-2 (170 mg, 0.999 mmol) dissolved in DCM (1.0 mL) was treated with hydroxylamine hydrochloride (69.4 mg, 0.999 mmol) followed by TEA (0.25 mL, 1.8 mmol) and stirred for 14 h. The reaction mixture was then partitioned between water and EtOAc. The organic portion was concentrated under reduced pressure and used without further manipulation as methyl (1R,3S)-3-((E)-(hydroxyimino)methyl)cyclohexane-1-carboxylate (185 mg, 0.999 mmol, 100% yield). LC-MS (M+H)=186.1; HPLC RT=0.96 min; Method A Intermediate 12-4

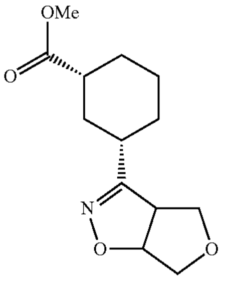 [SMILES: COC(=O)[C@@H]1CCC[C@H](C2=NOC3COCC23)C1]

A solution of 12-3 (0.19 g, 1.0 mmol) dissolved in DMF (5 mL) was treated with NCS (0.133 g, 0.999 mmol). After 3 h, the reaction mixture was partitioned between water and EtOAc. The organic portion was concentrated under reduced pressure then the residue, methyl (1R,3S)-3-((Z)-chloro(hydroxyimino)methyl)cyclohexane-1-carboxylate, dissolved in DCM (10 mL) was treated with 2,5-dihydrofuran (84 mg, 1.2 mmol) followed by TEA (2.0 mL, 14 mmol) and stirred for 14 h. The reaction mixture was concentrated under reduced pressure then the residue purified by silica gel chromatography (in-line light scattering detection) to afford methyl (1R,3S)-3-(3a,4,6,6a-tetrahydrofuro[3,4-d]isoxazol-3-yl)cyclohexane-1-carboxylate (53 mg, 0.21 mmol, 21% yield). LC-MS (M+H)=254.2: HPLC RT=0.96 min; Method A Intermediate 12-5

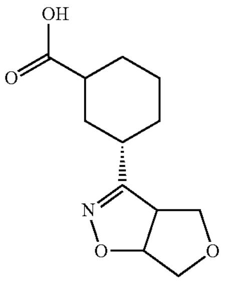 [SMILES: O=C(O)C1CCC[C@H](C2=NOC3COCC23)C1]

A solution of 12-4 (52 mg, 0.21 mmol) dissolved in THF (3.4 mL) with a few drops of MeOH was treated with LiOH (26 mg, 0.62 mmol) dissolved in water (0.7 mL) and the reaction mixture was stirred for 14 h. 1N HCl was added to the reaction mixture and the resulting solution was extracted with EtOAc. The organic portions were concentrated to afford (1R,3S)-3-(3a,4,6,6a-tetrahydrofuro[3,4-d]isoxazol-3-yl)cyclohexane-1-carboxylic acid (49 mg, 0.21 mmol, 100% yield). LC-MS (M+H)=240.2; HPLC RT=0.83 min; Method A Example 12: Prepared from intermediate 13-5 and IV-2a according to the general procedure detailed for Intermediate 1-1 to afford four isomeric products which were resolved with SFC separation: Preparative Chromatographic Conditions: Column: Chiral IC, 21×250 mm. 5 micron, Mobile Phase: 65% CO2/35% IPA w/0.1% DEA, Flow Conditions: 60 mL/min; Analytical Chromatographic Conditions (Before Prep): Column: Chiral IC, 4.6×150 mm, 5 micron, Mobile Phase: 65% CO2/35% IPA w/0.1% DEA RT (peak 1): 3.2 min, Peak 1 (Example 12, 1.7 mg, 2.8 μmol, 1.5% yield): LC-MS (M+H)=590.4, HPLC RT=2.53 min; Method C. $^1$H NMR (500 MHz, DMSO-d6) S 10.12 (s, 1H), 7.92 (br d, J=7.6 Hz, 1H), 7.83 (br d, J=4.3 Hz, 1H), 7.54 (br dd, J=5.0, 3.2 Hz, 1H), 7.23 (br t, J=9.8 Hz, 1H), 4.77 (dd, J=9.2, 3.4 Hz, 1H), 4.39 (d, J=9.5 Hz, 1H), 4.07-3.94 (m, 1H), 3.72 (br d, J=10.7 Hz, 2H), 3.50 (br t, J=7.6 Hz, 1H), 3.30-3.20 (m, 1H), 2.79 (br dd, J=10.7, 4.0 Hz, 1H), 2.67 (br s, 1H), 2.42 (br s, 1H), 2.31 (s, 1H), 2.19-1.99 (m, 2H), 1.73-1.59 (m, 3H), 1.57-1.47 (m, 3H), 1.31-0.97 (m, 6H), 0.85 (q, J=12.2 Hz, 1H), 0.53-0.41 (m, 2H) some protons obscured by solvent suppression.

RT (peak 2): 4.1 min, Example 13 (2.6 mg, 4.4 μmol, 2.4% yield), see table for characterization information.

RT (peak 3): 5.0 min, Example 14 (2.2 mg, 3.7 μmol, 2.0% yield), see table for characterization information.

RT (peak 4); 8.1 min, Example 15 (2.5 mg, 4.2 μmol, 2.3% yield), see table for characterization information.

Additional compounds of this invention are listed in Tables 2 and 3.

TABLE 2

| Ex. No, | Structure | Name | $^1$HNMR | LC RT/ Method | MS (ESI) m/z |
|---|---|---|---|---|---|
| 5 | 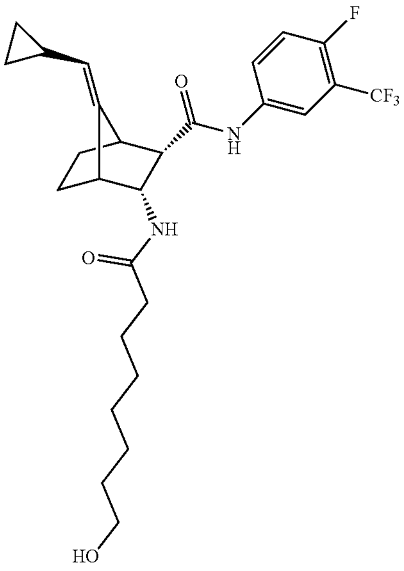 | (1R,2R,3R,4R,Z)-7-(cyclopropylmethylene)-N-(4-fluoro-3-(trifluoromethyl)phenyl)-3-(8-hydroxyoctanamido)bicyclo [2.2.1]heptane-2-carboxamide | $^1$H NMR (500 MHz, DMSO-d6) δ 10.10 (s, 1H), 7.90 (br d, J = 4.3 Hz, 1H), 7.77 (br d, J = 8.5 Hz, 1H), 7.49 (d, J = 8.3 Hz, 1H), 7.22 (t, J = 9.8 Hz, 1H), 4.38 (d, J = 9.5 Hz, 1H), 4.13-3.98 (m, 1H), 3.08 (q, J = 6.1 Hz, 1H), 2.94 (d, J = 4.9 Hz, 1H), 2.78 (br dd, J = 10.5, 4.1 Hz, 1H), 2.63 (br s, 1H), 2.40 (br s, 1H), 1.94-1.78 (m, 2H), 1.78-1.57 (m, 2H), 1.23 (br dd, J = 8.9, 4.6 Hz, 1H), 1.19-1.01 (m, 6H), 0.90 (br s, 6H), 0.53-0.39 (m, 2H), 0.11-0.02 (m, 2H). | 2.52/C | 580.1 |
| 6 | 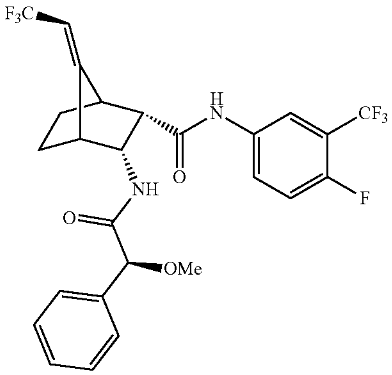 | (1R,2S,3R,4R,Z)-N-(4-fluoro-3-(trifluoromethyl)phenyl)-3-((S)-2-methoxy-2-phenylacetamido)-7-(2,2,2-trifluoroethylidene)bicyclo [2.2.1]heptane-2-carboxamide | $^1$H NMR (500 MHz, DMSO-d6) δ 10.62 (s, 1H), 9.17 (br d, J = 7.3 Hz, 1H), 8.10 (br d, J = 4.3 Hz, 1H), 7.93-7.75 (m, 1H), 7.53 (t, J = 9,6 Hz, 1H), 7.40-7.30 (m, 4H), 5.92 (q, J = 7.8 Hz, 1H), 4.69 (s, 1H), 4.33 (br s, 1H), 3.29 (s, 1H), 3.22 (br d, J = 11.0 Hz, 1H), 3.02-2.92 (m, 3H), 2.08-1.88 (m, 1H), 1.86-1.64 (m, 1H), 1.46 (br t. J = 14.2 Hz, 2H). | 2.55/C | 545.1 |
| 7 | 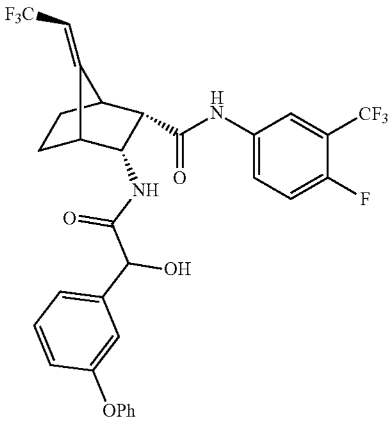 | (1R,2S,3R,4R,Z)-N-(4-fluoro-3-(trifluoromethyl)phenyl)-3-(2-hydroxy-2-(3-phenoxyphenyl)acetamido)-7-(2,2,2-trifluoroethylidene)bicyclo [2.2.1]heptane-2-carboxamide | $^1$H NMR (500 MHz, DMSO-d6) δ 10.61 (s, 1H), 9.28 (br d, J = 7.3 Hz, 1H), 8.00 (br d, J = 4.3 Hz, 1H), 7.76 (br d, J = 8.9 Hz, 1H), 7.46 (t, J = 9.6 Hz, 1H), 7.40-7.29 (m, 3H), 7.22-7.08 (m, 2H), 7.01-6.91 (m, 3H), 5.85 (q, J = 7.7 Hz, 1H), 4.88 (br s, 1H), 4.21 (br s, 1H), 3.80 (br d, J = 5.8 Hz, 1H), 3.24-3.04 (m, 1H), 2.91 (br d, J = 16.2 Hz, 2H), 1.88-1.71 (m, 1H), 1.69-1.51 (m, 1H), 1.44 (br s, 1H), 1.28 (br s, 1H). | 2.46/B | 623.2 |

TABLE 2-continued

| Ex. No, | Structure | Name | $^1$HNMR | LC RT/ Method | MS (ESI) m/z |
|---|---|---|---|---|---|
| 8 | 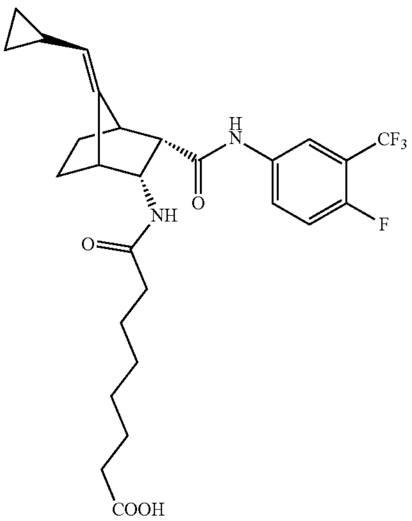 | 8-(((1R,2R,3S,4R,Z)-7-(cyclopropylmethylene)-3-((4-fluoro-3-(trifluoromethyl)phenyl) carbamoyl)bicyclo[2.2.1] heptan-2-yl)amino)-8-oxooctanoic acid | $^1$H NMR (500 MHz, DMSO-d6) δ 10.35 (s, 1H), 8.13 (br d, J = 4.0 Hz, 1H), 8.03 (br d, J = 8.2 Hz, 1H), 7.85-7.72 (m, 1H), 7.46 (t, J = 9.9 Hz, 1H), 4.62 (d, J = 9.8 Hz, 1H), 4.35 - 4.20 (m, 1H), 4.05 (s, 1H), 3.08-2.96 (m, 1H), 2.88 (br s, 1H), 2.64 (br s, 1H), 2.49-2.30 (m, 1H), 2.18-2.04 (m, 4H), 2.02-1.82 (m, 2H), 1.47 (dt, J = 8.4, 4.3 Hz, 1H), 1.43-1.30 (m, 5H), 1.16 (br s, 4H), 0.75-0.55 (m, 2H), 0.37-0.24 (m, 2H). | 2.25/C | 525.0 |

TABLE 3

| Ex. No. | Structure | Name | $^1$HNMR | LC RT/ Method | MS (ESI) m/z |
|---|---|---|---|---|---|
| 9 | 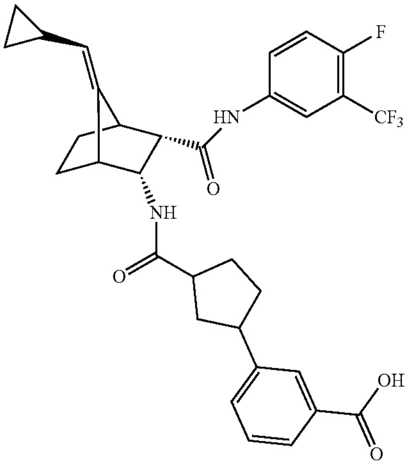 | 3-(3-{[(1R,2R,3S,4R,7Z)-3-{[4-fluoro-3-(trifluoromethyl)phenyl] carbamoyl}-7-(2,2,2-trifluoroethylidene)bicyclo[2.2.1] heptan-2-yl]carbamoyl}cyclopentyl) benzoic acid | 1H NMR (500 MHz, DMSO-d6) δ 10.50-10.29 (m, 1H), 8.21-8.04 (m, 2H), 7.80-7.59 (m, 3H), 7.42-7.22 (m, 3H), 5.87 (q, J = 7.9 Hz, 1H), 4.53-4.31 (m, 1H), 3.12 (br d, J = 10.4 Hz, 1H), 3.06-2.85 (m, 4H), 2.29-2.20 (m, 1H), 2.10-1.88 (m, 4H), 1.87-1.74 (m, 1H), 1.69-1.36 (m, 4H) | 2.38/C Separation: Chiral AS, 30 x 250 mm, 5 micron, Mobile Phase: 90% CO2/10% MeOH w/0.1% DE A, RT: 14.49 min | 613.2 |

TABLE 3-continued

| Ex. No. | Structure | Name | $^1$HNMR | LC RT/ Method | MS (ESI) m/z |
|---|---|---|---|---|---|
| 10 | 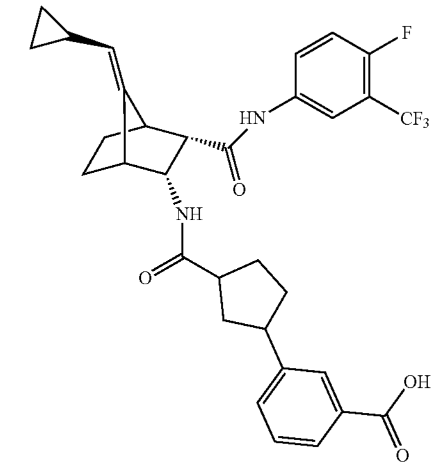 | 3-(3-{[(1R,2R,3S,4R.,7Z)-3-{[4-fluoro-3-(trifluoromethyl)phenyl]carbamoyl}-7-(2,2,2-trifluoroethylidene)bicyclo[2.2.1]heptan-2-yl]carbamoyl}cyclopentyl)benzoic acid | 1H NMR (500 MHz, DMSO-d6) δ 10.49 (s, 1H), 8.20 (br d, J = 7.8 Hz, 1H), 8.13 (br d, J = 4.7 Hz, 1H), 7.81-7.70 (m, 3H), 7.48 (t, J = 9.6 Hz, 1H), 7.41-7.32 (m, 2H), 5.87 (q, J = 7.9 Hz, 1H), 4.45-4.35 (m, 1H), 3.18 - 3.13 (m, 1H), 3.03-2.96 (m, 2H), 2.93-2.86 (m, 2H), 2.22-2.11 (m, 2H), 2.09-2.02 (m, 1H), 2.00-1.94 (m, 1H), 1.91-1.85 (m, 1H), 1.80-1.72 (m, 1H), 1.66-1.40 (m, 4H) | 1.99/C Separation: Chiral AS. 30 x 250 mm, 5 micron, Mobile Phase: 90% CO2/10% MeOH w/0.1% DEA, RT: 24.06 min | 613.1 |
| 11 | 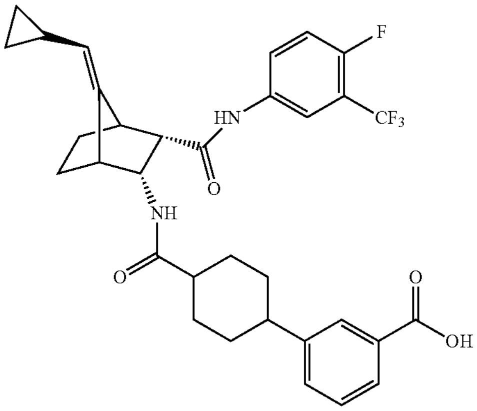 | 3-(4-{[(1R,2R,3S,4R,7Z)-3-{[4-fluoro-3-(trifluoromethyl)phenyl]carbamoyl}-7-(2,2,2-trifluorocthylidene)bicyclo[2.2.1]heptan-2-yl\|carbamoyl}cyclohexyl)benzoic acid | 1H NMR (500 MHz, DMSO-d6) δ 10.49 (s, 1H), 8.22 (br d, J = 7.9 Hz, 1H), 8.09 (dd, J = 6.4, 2.4 Hz, 1H), 7.81-7.62 (m, 3H), 7.46-7.27 (m, 3H), 5.89 (q, J = 7.8 Hz, 1H), 4.48-4.36 (m, 1H), 3.16 (br dd, J = 11.0, 4.0 Hz, 1H), 3.05 (br s, 1H), 2.93 (br s, 1H), 2.59 (br d, J = 4.0 Hz, 2H), 2.23-2.15 (m, 1H), 2.09-2.02 (m, 1H), 1.98-1.91 (m, 1H), 1,92-1.76 (m, 2H), 1.66-1.43 (m, 5H), 1.42-1.30 (m, 1H) some protons obscured by solvent supression | 1.99/C | 627.3 |
| 13 | 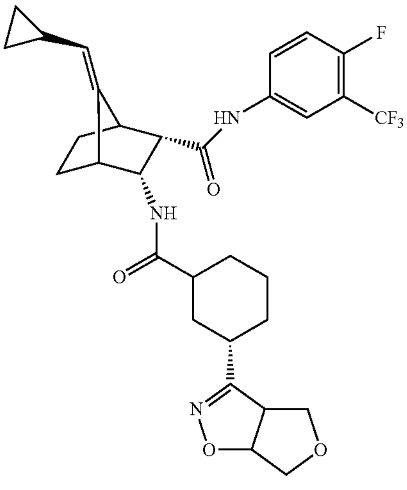 | (1R,2S,3R,4R,7Z)-3-[(3S)-3-{3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo[2.2.1]heptane-2-carboxamide | 1H NMR (500 MHz, DMSO-d6) δ 10.12 (s, 1H), 7.88 (br d, J = 7.6 Hz, 2H), 7.56-7.44 (m, 1H), 7.24 (br t, J = 9.6 Hz, 1H), 4.84 (dd, J = 9.2, 3.4 Hz, 1H), 4.39 (br d, J = 9.5 Hz, 1H), 4.10-4.01 (m, 1H), 3.85-3.66 (m, 3H), 3.38-3.27 (m, 1H), 2.85-2.74 (m, 1H), 2.65 (br s, 1H), 2.42 (br s, 1H), 2.21-2.14 (m, 1H), 2.09 (br t, J = 11.9 Hz, 1H), 1.82-1.63 (m, 3H), 1.56 (br d, J = 11.3 Hz, 1H), 1.50-1.36 (m, 2H), 1.27-0.79 (m, 8H), 0.55-0.41 (m, 2H), 0.09 (br d, J = 2.7 Hz, 2H) | 2.47/C See 13 for seperation conitions | 590.4 |

TABLE 3-continued

| Ex. No. | Structure | Name | $^1$HNMR | LC RT/ Method | MS (ESI) m/z |
|---|---|---|---|---|---|
| 14 | 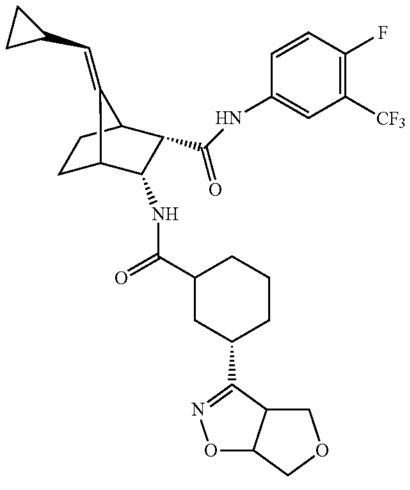 | (1R,2S,3R,4R,7Z)-3-[(3S)-3-{3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo[2.2.1]heptane-2-carboxamide | 1H NMR (500 MHz, DMSO-d6) δ 10.13 (s, 1H), 7.93 (br d, J = 7.6 Hz, 1H), 7.82-7.66 (m, 1H), 7.63-7.52 (m, 1H), 7.21 (br t, J = 9.8 Hz, 1H), 4.82 (br dd, J = 9.0, 3.5 Hz, 1H), 4.39 (br d, J = 9.8 Hz, 1H), 4.07-3.93 (m, 1H), 3.80-3.60 (m, 3H), 3.37-3.23 (m, 1H), 2.85-2.74 (m, 1H), 2.67 (br s, 1H), 2.46-2.38 (m, 1H), 2.17 (brt, J = 11.9 Hz, 1H), 2.11-1.98 (m, 1H), 1.75-1.48 (m, 6H), 1.32-0.98 (m, 6H), 0.86-0.74 (m, 1H), 0.47 (br t, J = 7.0 Hz, 2H), 0.08 (br d, J = 2.4 Hz, 2H) some protons obscured by solvent supression | 2.52/C | 590.1 |
| 15 | 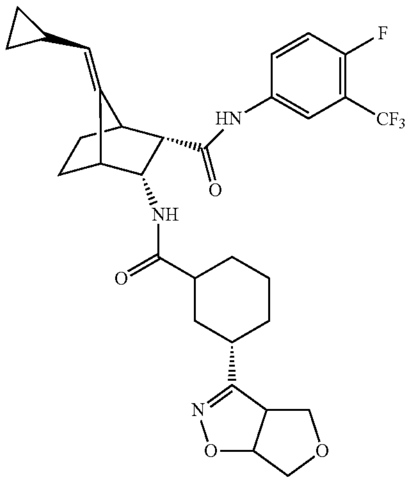 | (1R,2S,3R,4R,7Z)-3-[(3S)-3-{3aH,4H,6H,6aH-furo[3,4-d][1,2]oxazol-3-yl}cyclohexaneamido1-7-(cyclopropylmethylidene)-N-[4-fluoro-3-(trifluoromethyl)phenyl]bicyclo[2.2.1]heptane-2-carboxamide | 1H NMR (500 MHz, DMSO-d6) δ 10.38 (s, 1H), 8.21-8.02 (m, 2H), 7.84-7.68 (m, 1H), 7.47 (br t, J = 9.8 Hz, 1H), 5.08 (dd, J = 9.2, 3.7 Hz, 1H), 4.63 (d, J = 9.5 Hz, 1H), 4.25 (br d, J = 6.1 Hz, 1H), 4.10-3.93 (m, 3H), 3.60-3.52 (m, 1H), 3.44-3.38 (m, 1H), 3.03 (br dd, J = 10.5, 4.1 Hz, 1H), 2.91 (br s, 1H), 2.66 (br s, 1H), 2.48-2.40 (m, 1H), 2.34-2.24 (m, 1H), 1.97-1.82 (m, 4H), 1.76-1.58 (m, 2H), 1.51-1.24 (m, 5H), 1.22-1.10 (m, 1H), 1.06-0.92 (m, 1H), 0.78-0.66 (m, 2H), 0.32 (br d, J = 2.4 Hz, 2H) | 2.32/C | 590.0 |

TABLE 3-continued

| Ex. No. | Structure | Name | $^1$HNMR | LC RT/ Method | MS (ESI) m/z |
|---|---|---|---|---|---|
| 16 | 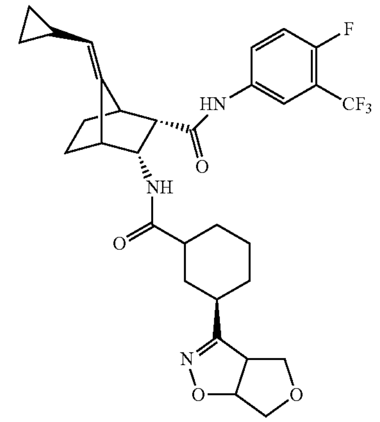 Preparative Chromatographic Conditions: Instrument: Waters 100 Prep SFC Column: Chiral IC, 21 x 250 mm. 5 micron Mobile Phase: 65% CO2/ 35% IPA w/0.1% DEA Flow Conditions: 60 mL/min RT = 3.2 min Analytical Chromatographic Conditions (Before Prep): Instrument: Shimadzu Nexera UC SFCColumn: Chiral IC, 4.6 x 150 mm, 5 micron Mobile Phase: 65% CO2/35% IPA w/0.1% DEA | (1R,2S,3R,4R,7Z)-3-[(3R)-3-{3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo[2.2.1]heptane-2-carboxamide | 1H NMR (500 MHz, DMSO-d6) δ 10.13 (br s, 1H), 7.92 (br d, J = 7.3 Hz, 1H), 7.88-7.75 (m, 1H), 7.54 (br d, J = 5.8 Hz, 1H), 7.24 (br d, J = 9.5 Hz, 1H), 4.78 (br d, J = 8.9 Hz, 1H), 4.39 (br d, J = 9.8 Hz, 1H), 4.01 (br s, 1H), 3.72 (br d, J = 9.5 Hz, 2H), 3.50 (br t, J = 7.5 Hz, 1H), 2.79 (br d. J = 10.4 Hz, 1H), 2.67 (br s, 1H), 2.42 (br s, 1H), 2.35-2.31 (m, 2H), 2.19-2.01 (m, 2H), 1.74-1.60 (m, 3H), 1.60-1.48 (m, 3H), 1.34-0.96 (m, 6H), 0.92-0.79 (m, 1H), 0.56-0.36 (m, 2H), 0.08 (br s, 2H) | 2.50/C | 590,4 |
| 17 | 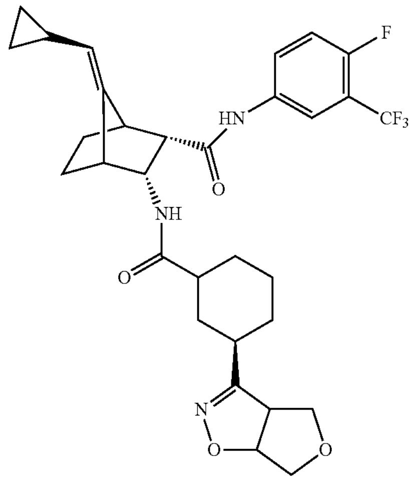 | (1R,2S,3R,4R,7Z)-3-[(3R)-3-(3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo[2.2.1]heptane-2-carboxamide | 1H NMR (500 MHz, DMSO-d6) δ 10.37 (s, 1H), 8.13 (br dd, J = 10.7, 7.6 Hz, 2H), 7.82-7.70 (m, 1H), 7.47 (br t, J = 9.8 Hz, 1H), 5.08 (br dd, J = 9.0, 3.5 Hz, 1H), 4.63 (br d, J = 9.5 Hz, 1H), 4.32-4.20 (m, 1H), 4.02-3.83 (m, 3H), 3.55 (br s, 2H), 3.18 (br d, J = 4.6 Hz, 1H), 3.03 (br dd, J = 10.7, 3.4 Hz, 1H), 2.89 (br s, 1H), 2.65 (br s, 1H), 2.45-2.30 (m, 2H), 2.04-1.87 (m, 2H), 1.81-1.59 (m, 3H), 1.53-1.03 (m, 7H), 0.78-0.61 (m, 2H), 0.32 (br s, 2H) | 2.38/C See example 17 for SFC separation RT = 4.1 | 589,9 |

TABLE 3-continued

| Ex. No. | Structure | Name | $^1$HNMR | LC RT/ Method | MS (ESI) m/z |
|---|---|---|---|---|---|
| 18 | 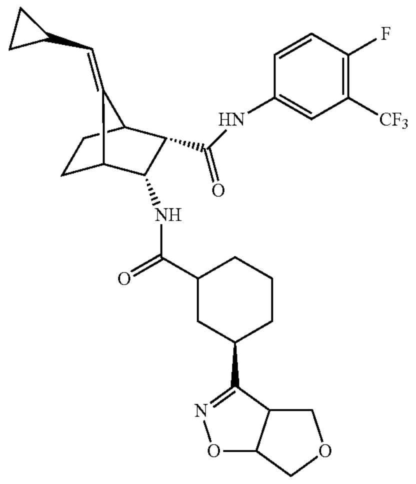 | (1R,2S,3R,4R,7Z)-3-[(3R)-3-{3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo [2.2.1]heptane-2-carboxamide | 1H NMR (500 MHz, DMSO-d6) δ 10.21-10.03 (m, 1H), 7.95-7.77 (m, 2H), 7.57-7.41 (m, 1H), 7.22 (br t, J = 9.7 Hz, 1H), 4.83 (dd, J = 9.2, 3.9 Hz, 1H), 4.45-4.31 (m, 1H), 4.10-3.95 (m, 1H), 3.86-3.62 (m, 3H), 3.38-3.25 (m, 1H), 3.19-3.06 (m, 1H), 2.87-2.77 (m, 1H), 2.66 (br t, J = 3.5 Hz, 1H), 2.48-2.35 (m, 1H), 2.23-2.12 (m, 2H), 2.10-1.99 (m, 1H), 1.75-1.56 (m, 4H), 1.52-1.32 (m, 2H), 1.30-0.98 (m, 5H), 0.96-0.85 (m, 1H), 0.82-0.66 (m, 1H), 0.60-0.38 (m, 2H) | 2.47/C See example 17 for SFC separation RT = 5.0 | 590.4 |
| 19 | 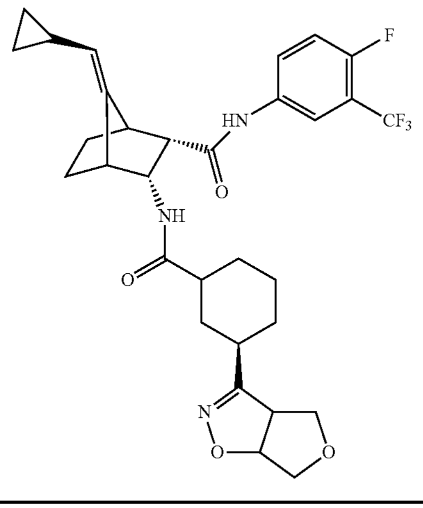 | (1R,2S,3R,4R,7Z)-3-[(3R)-3-(3aH,4H,6H,6aH-furo[3,4-d][1,2]oxazol-3-yl}cyclohexaneamido]-7-(cyclopropylmethylidene)-N-[4-fluoro-3-(trifluoromethyl)phenyl]bicyclo [2.2.1]heptane-2-carboxamide | 1H NMR (500 MHz, DMSO-d6) δ 10.47-10.25 (m, 1H), 8.17 (br d, J = 7.6 Hz, 1H), 8.01 (br d, J = 4.3 Hz, 1H), 7.89-7.78 (m, 1H), 7.46 (br t, J = 9.8 Hz, 1H), 5.07 (dd, J = 9.2, 3.7 Hz, 1H), 4.64 (d, J = 9.5 Hz, 1H), 4.28-4.19 (m, 1H), 4.06-3.83 (m, 3H), 3.60-3.50 (m, 1H), 3.08-3.00 (m, 1H), 2.92 (br s, 1H), 2.67 (br s, 1H), 2.47-2.23 (m, 2H), 1,99-1.67 (m, 6H), 1.55-1.22 (m, 6H), 1.19-1.11 (m, 1H), 1.10-0.92 (m, 1H), 0.72 (br t, J = 8.2 Hz, 2H), 0.33 (br d, J = 2.7 Hz, 2H) | 2.47/C See example 17 for SFC separation RT = 8.2 | 590.4 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound having Formula (I):

(I)

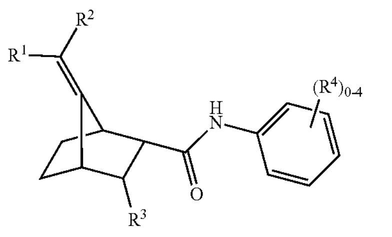

or a pharmaceutically acceptable salt thereof, wherein:

$R^1$ is halo, CN, $C_{1-7}$ alkyl substituted with 0-3 $R^6$, $C_{2-7}$ alkenyl substituted with 0-3 $R^6$, $C_{2-7}$ alkynyl substituted with 0-3 $R^6$, $C_{3-6}$ cycloalkyl substituted with 0-3 $R^{14}$, $C_{3-6}$ cycloalkenyl substituted with 0-3 $R^{14}$, aryl substituted with 0-3 $R^{14}$, or a 4- to 6-membered heterocyclyl comprising 1-3 heteroatoms selected from O, $S(=O)_p$, N, and $NR^{14a}$ and substituted with 0-3 $R^{14}$;

$R^2$ is H or $C_{1-3}$ alkyl;

$R^3$ is $—NR^aC(=O)R^5$, $—NR^aC(=O)(CR^dR^d)_{1-2}R^7$, or $—NR^aC(=O)NR^aR^7$;

$R^4$ is halo, CN, $C_{1-4}$ alkyl substituted with 0-5 halo substituents, —OH, $—OC_{1-4}$ alkyl substituted with 0-5 halo substituents, $—S(=O)_pR^c$, or aryl;

$R^5$ is $C_{1-8}$alkyl substituted with 0-4 $R^{11}$ or $C_{3-6}$cycloalkyl substituted with 0-4 $R^8$ and 0-2 $R^9$, $R^6$ is halo, OH, $C_{3-6}$ cycloalkyl, or aryl;

$R^7$ is aryl substituted with 0-4 $R^8$ and 0-2 $R^9$;

$R^8$ is $—OR^b$;

$R^9$ is halo, CN, phenyl substituted with 0-3 $R^{10}$ and 0-2 $R^{11}$, or 3- to 12-membered heterocyclyl comprising 1-5 heteroatoms selected from O, $S(=O)_p$, N, and $NR^{11a}$, and substituted with 0-3 $R^{10}$ and 0-2 $R^{11}$;

$R^{10}$ is halo, CN, or $C_{1-4}$ alkyl;

$R^{11}$ is $C_{1-3}$ alkyl substituted with 0-1 $R^{13}$ and 0-1 $R^{13}$, $—OR^b$, $—NR^aR^a$, $—NR^aC(=O)R^b$, $—NR^aC(=O)OR^b$, $—NR^aC(=O)NR^aR^a$, $—NR^aS(=O)_pR^c$, $—C(=O)R^b$, $—C(=O)OR^b$, $—C(=O)NR^aR^a$, $—C(=O)NR^aS(=O)_pR^c$, $—OC(=O)R^b$, $—S(=O)_pR^c$, $—S(=O)_pNR^aR^a$, $C_{3-10}$ carbocyclyl substituted with 0-5 $R^e$, 4- to 6-membered heterocyclyl comprising 1-4 heteroatoms selected from O, $S(=O)_p$, N and $NR^{15}$, and substituted with 0-5 $R^e$;

$R^{11a}$ is H, or $C_{1-4}$ alkyl substituted with 0-2 $R^e$;

$R^{12}$ is halo, $—C(=O)OR^b$, $—C(=O)NHR^a$, $—C(=O)NHOR^b$, or $C_{1-4}$ alkyl substituted with 0-3 halo or OH substituents;

$R^{13}$ is $—OR^b$, $—NR^aR^a$, $—NR^aC(=O)R^b$, $—NR^aC(=O)OR^b$, $—NR^aS(=O)_pR^c$, $—NR^aS(O)_pNR^aR^a$, $—OC(=O)NR^aR^a$, $—OC(=O)NR^aOR^b$, $—S(=O)_pNR^aR^a$, or $—S(O)_pR^c$;

$R^{14}$ is halo, CN, $C_{1-4}$ alkyl substituted with 0-3 halo substituents, $—OC_{1-4}$ alkyl substituted with 0-3 halo substituents, $—(CH_2)_{0-3}—NR^aR^a$, $—(CH_2)_{0-3}$-aryl substituted with 0-3 $R^e$, —O-aryl substituted with 0-3 $R^c$, or $—(CH_2)_{0-3}$-3- to 12-membered heterocyclyl comprising 1-4 heteroatoms selected from O, $S(=O)_p$, and N, and substituted with 0-3 $R^e$;

$R^{14a}$ is H, $C(=O)C_{1-4}$ alkyl, or $C_{1-3}$ alkyl substituted with 0-3 aryl substituents substituted with 0-2 halo substituents;

$R^{15}$ is H, $C_{1-3}$ alkyl, or aryl;

$R^{16}$ is $C_{1-3}$ alkyl substituted with 0-1 $R^e$, $—C(=O)R^b$, $—C(=O)OR^b$, $—C(=O)NR^aR^a$, $—C(=O)NR^aS(=O)_pR^c$, $—OC(=O)R^b$, $—S(=O)_pR^c$, or $—S(=O)_pNR^aR^a$;

$R^a$ is H, $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $—(CH_2)_n—C_{3-10}$ carbocyclyl substituted with 0-5 $R^e$, or $—(CH_2)_n$-3- to 12-membered heterocyclyl comprising 1-4 heteroatoms selected from O, $S(=O)_p$, and N, and substituted with 0-5 $R^e$; or $R^a$ and $R^a$ together with the nitrogen atom to which they are both attached form a 3- to 12-membered heterocyclyl comprising 1-4 heteroatoms selected from O, $S(=O)_p$, and N, and substituted with 0-5 $R^e$;

$R^b$ is H, $C_{1-5}$ alkyl substituted with 0-5 $R^e$, $C_{2-3}$ alkenyl substituted with 0-5 $R^e$, $C_{2-5}$ alkynyl substituted with 0-5 $R^e$, $—(CH_2)$, $—C_{3-10}$ carbocyclyl substituted with 0-5 $R^e$, or $—(CH_2)_n$-3- to 12-membered heterocyclyl comprising 1-4 heteroatoms selected from O, $S(=O)_p$, and N, and substituted with 0-5 $R^e$;

$R^c$ is $C_{1-5}$ alkyl substituted with 0-5 $R^e$, $C_{2-5}$ alkenyl substituted with 0-5 $R^e$, $C_{2-5}$ alkynyl substituted with 0-5 $R^e$, $C_{3-6}$ carbocyclyl, or 3- to 12-membered heterocyclyl comprising 1-4 heteroatoms selected from O, $S(=O)_p$, and N;

$R^d$ is H, $—OR^b$, or $C_{1-5}$ alkyl substituted with 0-5 $R^e$;

$R^e$ is halo, CN, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, $—(CH_2)_n—C_{3-10}$ carbocyclyl substituted with 0-5 $R^g$, $—(CH_2)_n$-3- to 12-membered heterocyclyl comprising 1-4 heteroatoms selected from O, $S(=O)_p$, and N, and substituted with 0-5 $R^g$, $—(CH_2)_nOR^f$, $—C(=O)OR^f$, $—C(=O)NR^fR^f$, $—NR^fC(=O)R^f$, $—S(=O)_pR^f$, $—NR^fC(=O)OR^f$, $—OC(=O)NR^fR^f$, or $—(CH_2)_nNR^fR^f$;

$R^f$ is H, $C_{1-5}$ alkyl, $C_{3-6}$, cycloalkyl, or aryl; or $R^f$ and $R^f$ together with the nitrogen atom to which they are both attached form a 3- to 12-membered heterocyclyl comprising 1-4 heteroatoms selected from O, $S(=O)_p$, and N;

$R^g$ is halo, CN, OH, $C_{1-6}$ alkyl, $C_{3-6}$ cycloalkyl, or aryl;

n is zero, 1, 2, or 3; and p is zero, 1, or 2.

2. The compound of claim 1, having Formula (II):

(II)

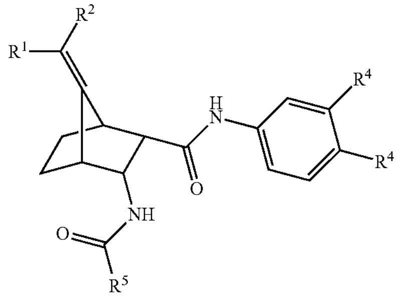

or a pharmaceutically acceptable salt thereof, wherein:

$R^1$ is halo, $C_{1-4}$ alkyl substituted with 0-4 halo, $C_{3-6}$ cycloalkyl, or phenyl;

$R^2$ is H;

$R^4$ is halo or $C_{1-4}$ alkyl substituted with 0-4 halo substituents;

$R^5$ is $C_{3-6}$cycloalkyl substituted with 0-1 $R^9$;

$R^9$ is halo, CN, or phenyl substituted with 0-1 $R^{10}$ and 0-1 $R^{11}$,

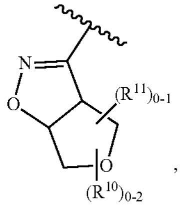

,

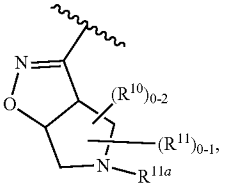

or

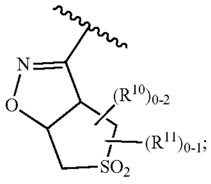

$R^{10}$ is halo, CN, or $C_{1-4}$ alkyl;

$R^{11}$ is —OH, —$OC_{1-4}$ alkyl, or —C(═O)$OR^b$;

$R^{11a}$ is H or $C_{1-3}$ alkyl;

$R^a$ is H or $C_{1-4}$ alkyl; and $R^b$ is H or $C_1$ alkyl.

3. The compound of claim 1, having Formula (II):

(II)

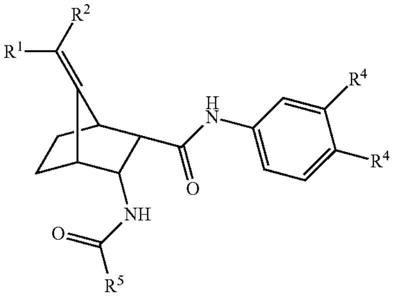

or a pharmaceutically acceptable salt thereof, wherein:

$R^1$ is halo, $C_{1-4}$ alkyl substituted with 0-4 halo substituents, $C_{3-6}$ cycloalkyl, or phenyl;

$R^2$ is H;

$R^4$ is halo or $C_{1-4}$ alkyl substituted with 0-4 halo substituents;

$R^5$ is $C_{1-7}$ alkyl substituted with 0-1 $R^{11}$;

$R^{11}$ is —$OR^b$, —C(═O)$R^b$, —C(═O)$OR^b$, or —C(═O)$NR^aR^a$;

$R^a$ is H or $C_{1-4}$ alkyl; and $R^b$ is H or $C_{1-4}$ alkyl.

4. The compound of claim 1, having Formula (III):

(III)

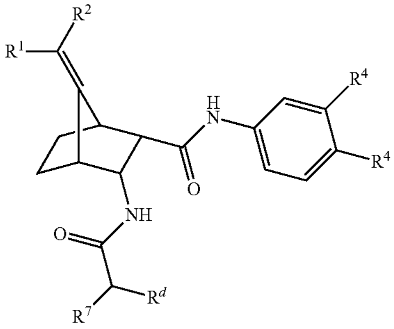

or a pharmaceutically acceptable salt thereof, wherein:

$R^1$ is halo, $C_{1-4}$ alkyl substituted with 0-4 halo substituents, $C_{3-6}$ cycloalkyl, or phenyl;

$R^2$ is H;

$R^4$ is halo or $C_{1-4}$ alkyl substituted with 0-4 halo substituents;

$R^7$ is aryl substituted with 0-1 $R^g$ and 0-1 $R^9$;

$R^8$ is —$OR^b$;

$R^9$ is halo, CN, or phenyl substituted with 0-3 $R^{10}$ and 0-2 $R^{11}$;

$R^{10}$ is halo, CN, $C_{1-4}$ alkyl, —OH, or —$OC_{1-4}$ alkyl;

$R^{11}$ is —$OR^1$ or —C(═O)$OR^b$;

$R^a$ is H or $C_{1-4}$ alkyl;

$R^b$ is H, $C_{1-4}$ alkyl, or phenyl; and $R^d$ is —OH or —$OC_{1-4}$ alkyl.

5. The compound of claim 2, having Formula (IV):

(IV)

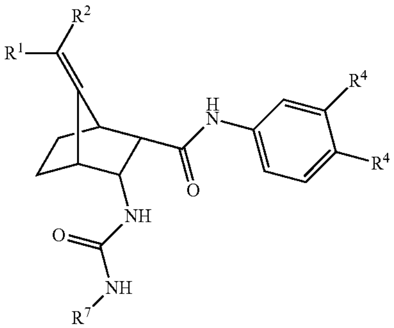

or a pharmaceutically acceptable salt thereof, wherein:

$R^1$ is halo, $C_{1-4}$ alkyl substituted with 0-4 halo substituents, $C_{3-6}$, cycloalkyl, or phenyl;

$R^2$ is H;

$R^4$ is halo or $C_{1-4}$ alkyl substituted with 0-4 halo substituents;

$R^7$ is aryl substituted with 0-1$R^8$ and 0-1 $R^9$;

$R^8$ is —$OC_{1-4}$ alkyl substituted with 0-5 halo or OH substituents;

$R^9$ is halo, CN, or phenyl substituted with 0-3 $R^{10}$ and 0-2 $R^{11}$;

$R^{10}$ is halo, CN, $C_{1-4}$ alkyl, —OH, or —$OC_{1-4}$ alkyl;

$R^{11}$ is —$OR^1$ or —C(═O)$OR^b$;

$R^a$ is H or $C_{1-4}$ alkyl; and $R^b$ is H, $C_{1-4}$ alkyl, or phenyl.

6. A pharmaceutical composition comprising a compound of claim 1, or a pharmaceutically acceptable salt thereof, and a pharmaceutically acceptable carrier.

* * * * *